US012076112B2

(12) United States Patent
Vatanparvar et al.

(10) Patent No.: US 12,076,112 B2
(45) Date of Patent: *Sep. 3, 2024

(54) SYSTEM AND METHOD FOR CONDUCTING ON-DEVICE SPIROMETRY TEST

(71) Applicant: Samsung Electronics Co., Ltd., Suwon-si (KR)

(72) Inventors: Korosh Vatanparvar, Santa Clara, CA (US); Viswam Nathan, Mountain View, CA (US); Md Mahbubur Rahman, San Jose, CA (US); Ebrahim Nematihosseinabadi, Santa Clara, CA (US); Jilong Kuang, San Jose, CA (US); Jun Gao, San Jose, CA (US)

(73) Assignee: Samsung Electronics Co., Ltd., Suwon-si (KR)

( * ) Notice: Subject to any disclaimer, the term of this patent is extended or adjusted under 35 U.S.C. 154(b) by 1051 days.

This patent is subject to a terminal disclaimer.

(21) Appl. No.: 16/947,837

(22) Filed: Aug. 19, 2020

(65) Prior Publication Data

US 2021/0244313 A1    Aug. 12, 2021

Related U.S. Application Data

(63) Continuation-in-part of application No. 16/786,801, filed on Feb. 10, 2020, now Pat. No. 11,890,078.

(51) Int. Cl.
*A61B 5/00* (2006.01)
*A61B 5/087* (2006.01)
(Continued)

(52) U.S. Cl.
CPC .......... *A61B 5/0077* (2013.01); *A61B 5/0871* (2013.01); *A61B 5/091* (2013.01);
(Continued)

(58) Field of Classification Search
CPC ..... A61B 5/0077; A61B 5/0871; A61B 5/091; A61B 5/1032; A61B 5/486; A61B 5/6898;
(Continued)

(56) References Cited

U.S. PATENT DOCUMENTS

| 7,447,333 | B1 * | 11/2008 | Masticola | .............. G16H 50/80 382/128 |
|---|---|---|---|---|
| 9,993,193 | B2 | 6/2018 | Van Vugt et al. | |

(Continued)

FOREIGN PATENT DOCUMENTS

| CN | 105286869 A | * | 2/2016 |
|---|---|---|---|
| CN | 108968962 A | | 12/2018 |

(Continued)

OTHER PUBLICATIONS

English Translation of JPH0993316A (Year: 1997).*

(Continued)

*Primary Examiner* — Angela M Hoffa
*Assistant Examiner* — Helene Bor

(57) ABSTRACT

A method includes receiving, by an electronic device, sensor data during a spirometry test of a user, the sensor data comprising audio data of the user, image data of a face of the user, and distance data of a distance from the face of the user. The method also includes obtaining, by the electronic device, at least one measured parameter associated with the spirometry test that is determined using at least one of the audio data, the image data, or the distance data, wherein the at least one measured parameter is correlated with an amount of air volume exchange or an amount of exhalation force by the user during the spirometry test. The method further includes providing, by the electronic device, real time feedback during the spirometry test, the real time feedback based on the at least one measured parameter, the (Continued)

real time feedback indicating whether or not the user is performing the spirometry test correctly.

20 Claims, 15 Drawing Sheets

(51) Int. Cl.
*A61B 5/091* (2006.01)
*A61B 5/103* (2006.01)
*A61B 7/00* (2006.01)
*G06V 10/764* (2022.01)
*G06V 40/16* (2022.01)
*G06V 40/18* (2022.01)
*H04R 1/40* (2006.01)
*H04R 3/00* (2006.01)
*H04R 5/027* (2006.01)
*H04S 3/00* (2006.01)

(52) U.S. Cl.
CPC ............ *A61B 5/1032* (2013.01); *A61B 5/486* (2013.01); *A61B 5/6898* (2013.01); *A61B 5/7221* (2013.01); *A61B 5/7405* (2013.01); *A61B 5/742* (2013.01); *A61B 5/7455* (2013.01); *A61B 7/003* (2013.01); *G06V 10/764* (2022.01); *G06V 40/171* (2022.01); *G06V 40/193* (2022.01); *H04R 1/406* (2013.01); *H04R 3/005* (2013.01); *H04R 5/027* (2013.01); *H04S 3/008* (2013.01); *H04R 2499/11* (2013.01); *H04S 2400/01* (2013.01); *H04S 2400/15* (2013.01)

(58) Field of Classification Search
CPC ..... A61B 5/7221; A61B 5/7405; A61B 5/742; A61B 5/7455; A61B 7/003; G06V 40/171; G06V 40/193; G06V 10/764; H04R 1/406; H04R 3/005; H04R 5/027; H04R 2499/11; H04S 3/008; H04S 2400/01; H04S 2400/15
See application file for complete search history.

(56) References Cited

U.S. PATENT DOCUMENTS

| | | | |
|---|---|---|---|
| 10,028,675 | B2 | 7/2018 | Patel et al. |
| 2005/0124375 | A1 | 6/2005 | Nowosielski |
| 2006/0106601 | A1* | 5/2006 | Kong .................. G10L 21/0208 704/226 |
| 2008/0019548 | A1* | 1/2008 | Avendano ............. H04R 3/005 381/313 |
| 2011/0158425 | A1* | 6/2011 | Hayakawa .......... H04M 1/6008 381/92 |
| 2012/0041279 | A1* | 2/2012 | Freeman ................ G16Z 99/00 600/534 |
| 2013/0079658 | A1* | 3/2013 | Cardoso ............... G01N 33/497 600/532 |
| 2013/0184540 | A1 | 7/2013 | Boschetti Sacco et al. |
| 2015/0216448 | A1 | 8/2015 | Lotan et al. |
| 2015/0265187 | A1 | 9/2015 | Bernal et al. |
| 2017/0161720 | A1 | 6/2017 | Xing et al. |
| 2017/0273597 | A1* | 9/2017 | Schuelke ............. A61B 5/7405 |
| 2018/0092595 | A1 | 4/2018 | Chen et al. |
| 2019/0038216 | A1* | 2/2019 | Ser ......................... G16H 50/20 |

FOREIGN PATENT DOCUMENTS

| | | | |
|---|---|---|---|
| JP | H0993316 A | * | 4/1997 |
| JP | 2005519686 A | | 7/2005 |
| JP | 4557059 B2 | | 10/2010 |
| JP | 2015536691 A | | 12/2015 |
| WO | 2016072948 A1 | | 5/2016 |
| WO | 2017136639 A1 | | 8/2017 |
| WO | 2018/170009 A1 | | 9/2018 |

OTHER PUBLICATIONS

International Search Report and Written Opinion of the International Searching Authority dated Mar. 22, 2021 in connection with International Application No. PCT/KR2020/017410, 12 pages.
Non-Final Office Action dated Sep. 21, 2022 in connection with U.S. Appl. No. 16/786,801, 44 pages.
Notice of Allowance dated Sep. 26, 2023 in connection with U.S. Appl. No. 16/786,801, 15 pages.

* cited by examiner

SYSTEM AND METHOD FOR CONDUCTING ON-DEVICE SPIROMETRY TEST

CROSS-REFERENCE TO RELATED APPLICATIONS AND CLAIM OF PRIORITY

This application is a continuation-in-part of U.S. patent application Ser. No. 16/786,801 entitled "SYSTEM AND METHOD FOR CONDUCTING ON-DEVICE SPIROMETRY TEST," filed Feb. 10, 2020, the contents of which are incorporated herein by reference.

TECHNICAL FIELD

This disclosure relates generally to health monitoring systems and methods. More specifically, this disclosure relates to a system and method for conducting an on-device, effort-aware spirometry test.

BACKGROUND

Chronic respiratory diseases (chronic diseases of the airways) currently affect an estimated 40 million people in the United States alone and are the third leading cause of death. Common respiratory diseases include asthma, chronic obstructive pulmonary disease (COPD), occupational lung disease, and chronic bronchitis. These diseases can cause increased inflammation and mucus in the lungs, narrow or swollen airways, and partial blocking of airflow. One test that is commonly used in diagnosis and treatment of chronic respiratory diseases is spirometry. Spirometry is a pulmonary function test that can be used to diagnose breathing conditions, periodically monitor lung conditions, determine whether medications are working, and reduce chronic respiratory morbidity.

SUMMARY

This disclosure provides a system and method for conducting an on-device, effort-aware spirometry test.

In a first embodiment, a method includes receiving, by an electronic device, sensor data during a spirometry test of a user, the sensor data comprising audio data of the user, image data of a face of the user, and distance data of a distance from the face of the user. The method also includes obtaining, by the electronic device, at least one measured parameter associated with the spirometry test that is determined using at least one of the audio data, the image data, or the distance data, wherein the at least one measured parameter is correlated with an amount of air volume exchange or an amount of exhalation force by the user during the spirometry test. The method further includes providing, by the electronic device, real time feedback during the spirometry test, the real time feedback based on the at least one measured parameter, the real time feedback indicating whether or not the user is performing the spirometry test correctly.

In a second embodiment, an electronic device includes at least one sensor and a processor. The processor is configured to receive sensor data obtained by the at least one sensor during a spirometry test of a user, the sensor data comprising audio data of the user, image data of a face of the user, and distance data of a distance from the face of the user. The processor is also configured to obtain at least one measured parameter associated with the spirometry test that is determined using at least one of the audio data, the image data, or the distance data, wherein the at least one measured parameter is correlated with an amount of air volume exchange or an amount of exhalation force by the user during the spirometry test. The processor is further configured to control the electronic device to provide real time feedback during the spirometry test, the real time feedback based on the at least one measured parameter, the real time feedback indicating whether or not the user is performing the spirometry test correctly.

In a third embodiment, a non-transitory computer readable medium contains computer readable program code that, when executed, causes at least one processor of an electronic device to receive sensor data during a spirometry test of a user, the sensor data comprising audio data of the user, image data of a face of the user, and distance data of a distance from the face of the user; obtain at least one measured parameter associated with the spirometry test that is determined using at least one of the audio data, the image data, or the distance data, wherein the at least one measured parameter is correlated with an amount of air volume exchange or an amount of exhalation force by the user during the spirometry test; and control the electronic device to provide real time feedback during the spirometry test, the real time feedback based on the at least one measured parameter, the real time feedback indicating whether or not the user is performing the spirometry test correctly.

Other technical features may be readily apparent to one skilled in the art from the following figures, descriptions, and claims.

Before undertaking the DETAILED DESCRIPTION below, it may be advantageous to set forth definitions of certain words and phrases used throughout this patent document. The terms "transmit," "receive," and "communicate," as well as derivatives thereof, encompass both direct and indirect communication. The terms "include" and "comprise," as well as derivatives thereof, mean inclusion without limitation. The term "or" is inclusive, meaning and/or. The phrase "associated with," as well as derivatives thereof, means to include, be included within, interconnect with, contain, be contained within, connect to or with, couple to or with, be communicable with, cooperate with, interleave, juxtapose, be proximate to, be bound to or with, have, have a property of, have a relationship to or with, or the like.

Moreover, various functions described below can be implemented or supported by one or more computer programs, each of which is formed from computer readable program code and embodied in a computer readable medium. The terms "application" and "program" refer to one or more computer programs, software components, sets of instructions, procedures, functions, objects, classes, instances, related data, or a portion thereof adapted for implementation in a suitable computer readable program code. The phrase "computer readable program code" includes any type of computer code, including source code, object code, and executable code. The phrase "computer readable medium" includes any type of medium capable of being accessed by a computer, such as read only memory (ROM), random access memory (RAM), a hard disk drive, a compact disc (CD), a digital video disc (DVD), or any other type of memory. A "non-transitory" computer readable medium excludes wired, wireless, optical, or other communication links that transport transitory electrical or other signals. A non-transitory computer readable medium includes media where data can be permanently stored and media where data can be stored and later overwritten, such as a rewritable optical disc or an erasable memory device.

As used here, terms and phrases such as "have," "may have," "include," or "may include" a feature (like a number, function, operation, or component such as a part) indicate the existence of the feature and do not exclude the existence of other features. Also, as used here, the phrases "A or B," "at least one of A and/or B," or "one or more of A and/or B" may include all possible combinations of A and B. For example, "A or B," "at least one of A and B," and "at least one of A or B" may indicate all of (1) including at least one A, (2) including at least one B, or (3) including at least one A and at least one B.

As used here, the terms "first" and "second" may modify various components regardless of importance and do not limit the components. These terms are only used to distinguish one component from another. For example, a first user device and a second user device may indicate different user devices from each other, regardless of the order or importance of the devices. A first component may be denoted a second component and vice versa without departing from the scope of this disclosure.

It will be understood that, when an element (such as a first element) is referred to as being (operatively or communicatively) "coupled with/to" or "connected with/to" another element (such as a second element), it can be coupled or connected with/to the other element directly or via a third element. In contrast, it will be understood that, when an element (such as a first element) is referred to as being "directly coupled with/to" or "directly connected with/to" another element (such as a second element), no other element (such as a third element) intervenes between the element and the other element.

As used here, the phrase "configured (or set) to" may be interchangeably used with the phrases "suitable for," "having the capacity to," "designed to," "adapted to," "made to," or "capable of" depending on the circumstances. The phrase "configured (or set) to" does not essentially mean "specifically designed in hardware to." Rather, the phrase "configured to" may mean that a device can perform an operation together with another device or parts. For example, the phrase "processor configured (or set) to perform A, B, and C" may mean a generic-purpose processor (such as a CPU or application processor) that may perform the operations by executing one or more software programs stored in a memory device or a dedicated processor (such as an embedded processor) for performing the operations.

The terms and phrases as used here are provided merely to describe some embodiments of this disclosure but not to limit the scope of other embodiments of this disclosure. It is to be understood that the singular forms "a," "an," and "the" include plural references unless the context clearly dictates otherwise. All terms and phrases, including technical and scientific terms and phrases, used here have the same meanings as commonly understood by one of ordinary skill in the art to which the embodiments of this disclosure belong. It will be further understood that terms and phrases, such as those defined in commonly-used dictionaries, should be interpreted as having a meaning that is consistent with their meaning in the context of the relevant art and will not be interpreted in an idealized or overly formal sense unless expressly so defined here. In some cases, the terms and phrases defined here may be interpreted to exclude embodiments of this disclosure.

Examples of an "electronic device" according to embodiments of this disclosure may include at least one of a smart phone, a tablet personal computer (PC), a mobile phone, a video phone, an e-book reader, a desktop PC, a laptop computer, a netbook computer, a workstation, a personal digital assistant (PDA), a portable multimedia player (PMP), an MP3 player, a mobile medical device, a camera, or a wearable device (such as smart glasses, a head-mounted device (HMD), electronic clothes, an electronic bracelet, an electronic necklace, an electronic appcessory, an electronic tattoo, a smart mirror, or a smart watch). Other examples of an electronic device include a smart home appliance. Examples of the smart home appliance may include at least one of a television, a digital video disc (DVD) player, an audio player, a refrigerator, an air conditioner, a cleaner, an oven, a microwave oven, a washer, a drier, an air cleaner, a set-top box, a home automation control panel, a security control panel, a TV box (such as SAMSUNG HOMESYNC, APPLETV, or GOOGLE TV), a gaming console (such as an XBOX, PLAYSTATION, or NINTENDO), an electronic dictionary, an electronic key, a camcorder, or an electronic picture frame. Still other examples of an electronic device include at least one of various medical devices (such as diverse portable medical measuring devices (like a blood sugar measuring device, a heartbeat measuring device, or a body temperature measuring device), a magnetic resource angiography (MRA) device, a magnetic resource imaging (MRI) device, a computed tomography (CT) device, an imaging device, or an ultrasonic device), a navigation device, a global positioning system (GPS) receiver, an event data recorder (EDR), a flight data recorder (FDR), an automotive infotainment device, a sailing electronic device (such as a sailing navigation device or a gyro compass), avionics, security devices, vehicular head units, industrial or home robots, automatic teller machines (ATMs), point of sales (POS) devices, or Internet of Things (IOT) devices (such as a bulb, various sensors, electric or gas meter, sprinkler, fire alarm, thermostat, street light, toaster, fitness equipment, hot water tank, heater, or boiler). Other examples of an electronic device include at least one part of a piece of furniture or building/structure, an electronic board, an electronic signature receiving device, a projector, or various measurement devices (such as devices for measuring water, electricity, gas, or electromagnetic waves). Note that, according to embodiments of this disclosure, an electronic device may be one or a combination of the above-listed devices. According to some embodiments of this disclosure, the electronic device may be a flexible electronic device. The electronic device disclosed here is not limited to the above-listed devices and may include new electronic devices depending on the development of technology.

In the following description, electronic devices are described with reference to the accompanying drawings, according to embodiments of this disclosure. As used here, the term "user" may denote a human or another device (such as an artificial intelligent electronic device) using the electronic device.

Definitions for other certain words and phrases may be provided throughout this patent document. Those of ordinary skill in the art should understand that in many if not most instances, such definitions apply to prior as well as future uses of such defined words and phrases.

None of the description in this application should be read as implying that any particular element, step, or function is an essential element that must be included in the claim scope. The scope of patented subject matter is defined only by the claims. Moreover, none of the claims is intended to invoke 35 U.S.C. § 112(f) unless the exact words "means for" are followed by a participle. Use of any other term, including without limitation "mechanism," "module," "device," "unit," "component," "element," "member," "apparatus," "machine," "system," "processor," or "controller," within a claim is understood by the Applicant to refer to structures known to those skilled in the relevant art and is not intended to invoke 35 U.S.C. § 112(f).

BRIEF DESCRIPTION OF THE DRAWINGS

For a more complete understanding of this disclosure and its advantages, reference is now made to the following description, taken in conjunction with the accompanying drawings, in which.

DETAILED DESCRIPTION

Figure 1:
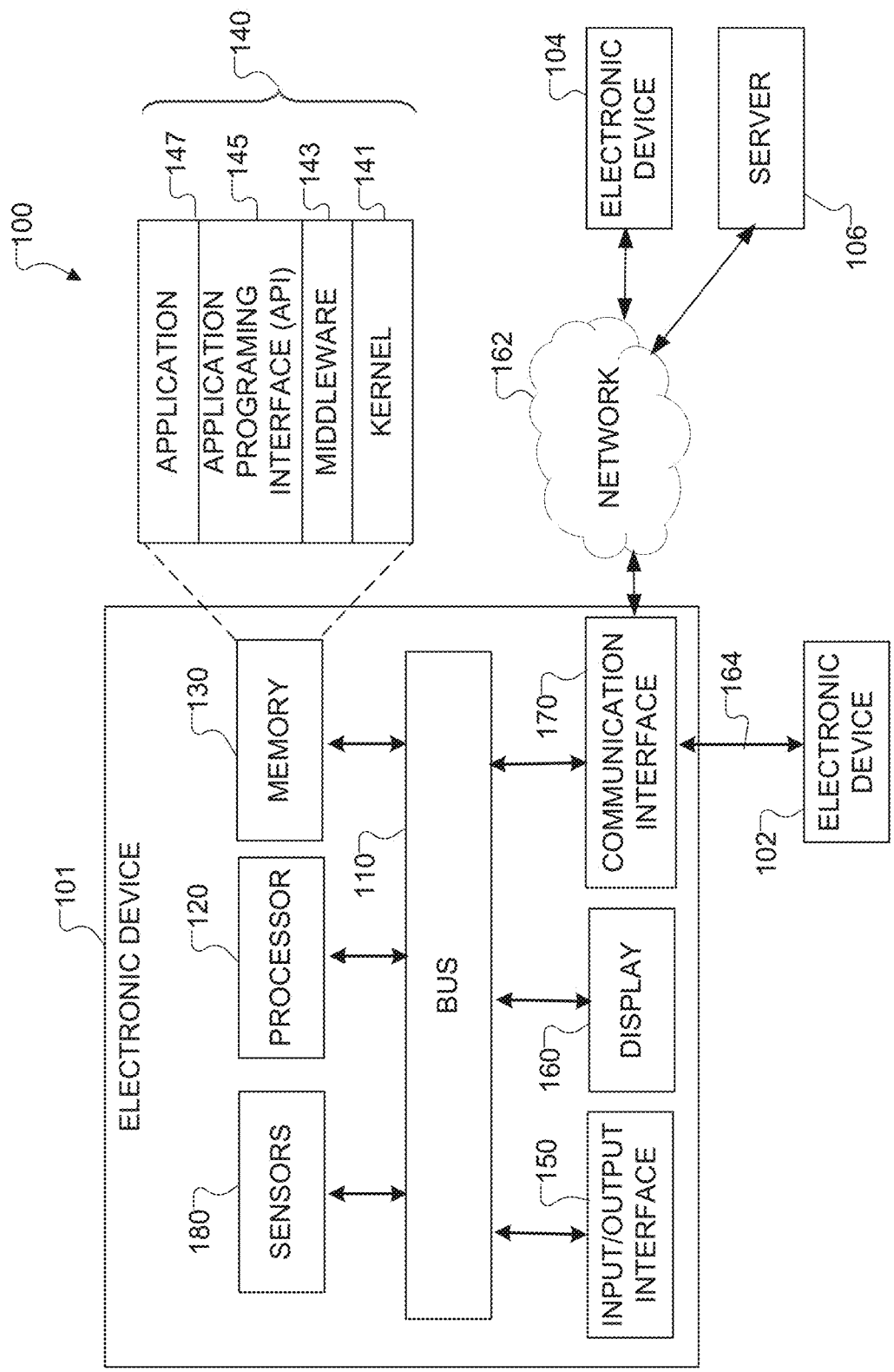
FIG. 1 illustrates an example network configuration in accordance with this disclosure.

The figures discussed below and the various embodiments used to describe the principles of this disclosure in this patent document are by way of illustration only and should not be construed in any way to limit the scope of the disclosure. Those skilled in the art will understand that the principles of this disclosure can be implemented in any suitably arranged system.

It is estimated that 235 million people in the world suffer from asthma, and that more than 250 million people have Chronic Obstructive Pulmonary Disease (COPD). Asthma is a condition in which the person's airways narrow and swell and produce extra mucus. This can make breathing difficult and trigger coughing, wheezing and shortness of breath. COPD is an umbrella term used to describe progressive lung diseases including emphysema, chronic bronchitis, pulmonary fibrosis, and refractory (non-reversible) asthma. These diseases are mainly characterized by increasing breathlessness.

Many asthma attacks have the potential to be life-threatening. Fatal asthma can occur in anyone with mild intermittent to more severe asthma. COPD is the third leading cause of death by disease in the United States; COPD also can cause serious long-term disability and early death. At the present time there is no cure, and the number of people dying from COPD is growing. However, in many cases, these diseases can be found early, and much can be done to treat and help manage the diseases.

Spirometry is used to diagnose conditions that affect breathing such as asthma and COPD. Moreover, spirometry may be used periodically to monitor a person's lung condition and check whether a treatment for a chronic lung condition is helping the person breathe better. Regular tracking of a patient's pulmonary function and health condition is important to prevent any significant lung deterioration or severe exacerbation, especially for already-diagnosed pulmonary patients. Spirometry may also be used periodically to check how well a patient's medications are working and whether the patient's breathing problems are under control. There is some evidence that application of spirometry testing in general practice may reduce the number of undetected cases with chronic respiratory morbidity as well as diagnostic misclassification, which may lead to overall improved respiratory health.

There is a correlation between a person's lung function and capacity and their overall physical endurance and health. For instance, athletes have larger lung capacity and higher expiratory air flow compared to non-athlete healthy people. Therefore, spirometry has been also utilized by general population and athletes as well, to evaluate and monitor their ventilatory function, lung capacity, and physical endurance regularly. With an increasing population regularly engaged in sports and exercise, this information can be utilized to provide feedback and adjust their daily physical or sports activity.

Current spirometry tests are typically performed in a medical office using dedicated, medical grade equipment. The subjects are required to blow into a device as hard as possible in order to measure the air flow and volume figures. In-office spirometry tests can require frequent clinic visits by the patient, which can be costly and inconvenient, especially for maintaining a regular tracking of their lung function. Such in-office tests also can require expensive medical equipment and must be attended by a medical professional to ensure that the test is performed correctly. Despite the presence of a medical professional, some tests are incorrectly performed and generate suboptimal results, such as when the patient does not exhale forcefully enough or for long enough.

Recently, FDA-approved portable devices have become available which can provide some of the same functionality of the in-clinic medical devices. Patients are able to use these devices in their home and conduct the spirometry test on their own. However, the limited availability and high cost of these devices still pose challenges for some patients to utilize them on a daily basis. Moreover, as the test is an intrinsically challenging task, many patients cannot always correctly perform the test without sufficient pre-training, thereby failing the test or getting inaccurate results. For example, the distance between the device and the patient and the openness of the patient's mouth can influence the audio features and thereby the test results.

To address these and other issues, embodiments of this disclosure provide systems and methods for a portable spirometry test that can be performed conveniently at any time and in any location using a smart phone or a wearable device such as a smart watch. For example, a patient can use their own device and conduct the spirometry test at their home. In some embodiments, the patient conducts the spirometry test while holding the device as they would do in a medical setting. The patient deeply inhales and forcefully exhales facing the camera and microphone of the device. The device then records audio captured by the microphone, mouth and face images captured by one or more cameras, and measured distance of the patient's face from the device. The combination of image, audio, and distance from the patient's face can be used to compensate for different subject variations (e.g., face/mouth structure, distance, etc.) encountered while taking the test. Moreover, the extracted data enables the device to quantify the effort of the patient during the test, compare to their maximum baseline, and validate the correctness of the test. Therefore, while performing the test, the patient can be guided using visual, audio, or haptic feedback to help them correctly accomplish the test.

FIG. 1 illustrates an example network configuration 100 in accordance with this disclosure. As shown in FIG. 1, according to embodiments of this disclosure, an electronic device 101 is included in the network configuration 100. The electronic device 101 may include at least one of a bus 110, a processor 120, a memory 130, an input/output (I/O) interface 150, a display 160, a communication interface 170, or a sensor 180. In some embodiments, the electronic device 101 may exclude at least one of the components or may add another component.

The bus 110 may include a circuit for connecting the components 120-180 with one another and transferring communications (such as control messages and/or data) between the components. The processor 120 may include one or more of a central processing unit (CPU), an application processor (AP), or a communication processor (CP). The processor 120 may perform control on at least one of the other components of the electronic device 101 and/or perform an operation or data processing relating to communication.

The memory 130 may include a volatile and/or non-volatile memory. For example, the memory 130 may store commands or data related to at least one other component of the electronic device 101. According to embodiments of this disclosure, the memory 130 may store software and/or a program 140. The program 140 may include, for example, a kernel 141, middleware 143, an application programming interface (API) 145, and/or an application program (or "application") 147. At least a portion of the kernel 141, middleware 143, or API 145 may be denoted an operating system (OS).

The kernel 141 may control or manage system resources (such as the bus 110, processor 120, or memory 130) used to perform operations or functions implemented in other programs (such as the middleware 143, API 145, or application program 147). The kernel 141 may provide an interface that allows the middleware 143, API 145, or application 147 to access the individual components of the electronic device 101 to control or manage the system resources. The middleware 143 may function as a relay to allow the API 145 or the application 147 to communicate data with the kernel 141, for example. A plurality of applications 147 may be provided. The middleware 143 may control work requests received from the applications 147, such as by allocating the priority of using the system resources of the electronic device 101 (such as the bus 110, processor 120, or memory 130) to at least one of the plurality of applications 147. The API 145 is an interface allowing the application 147 to control functions provided from the kernel 141 or the middleware 143. For example, the API 133 may include at least one interface or function (such as a command) for file control, window control, image processing, or text control.

The input/output interface 150 may serve as an interface that may, for example, transfer commands or data input from a user or other external devices to other component(s) of the electronic device 101. Further, the input/output interface 150 may output commands or data received from other component(s) of the electronic device 101 to the user or the other external devices.

The display 160 may include, for example, a liquid crystal display (LCD), a light emitting diode (LED) display, an organic light emitting diode (OLED) display, an active matrix OLED (AMOLED), a microelectromechanical systems (MEMS) display, or an electronic paper display. The display 160 can also be a depth-aware display, such as a multi-focal display. The display 160 may display various contents (such as text, images, videos, icons, or symbols) to the user. The display 160 may include a touchscreen and may receive, for example, a touch, gesture, proximity, or hovering input using an electronic pen or a body portion of the user.

The communication interface 170 may set up communication between the electronic device 101 and an external electronic device (such as a first electronic device 102, a second electronic device 104, or a server 106). For example, the communication interface 170 may be connected with a network 162 or 164 through wireless or wired communication to communicate with the external electronic device.

The electronic device 101 further includes one or more sensors 180 that can meter a physical quantity or detect an activation state of the electronic device 101 and convert metered or detected information into an electrical signal. For example, one or more sensors 180 can include one or more buttons for touch input, one or more cameras, a gesture sensor, a gyroscope or gyro sensor, an air pressure sensor, a magnetic sensor or magnetometer, an acceleration sensor or accelerometer, a grip sensor, a proximity sensor, a color sensor (such as a red green blue (RGB) sensor), a bio-physical sensor, a temperature sensor, a humidity sensor, an illumination sensor, an ultraviolet (UV) sensor, an electromyography (EMG) sensor, an electroencephalogram (EEG) sensor, an electrocardiogram (ECG) sensor, an infrared (IR) sensor, an ultrasound sensor, an iris sensor, or a fingerprint sensor. The sensor(s) 180 can also include an inertial measurement unit, which can include one or more accelerometers, gyroscopes, and other components. The sensor(s) 180 can further include a control circuit for controlling at least one of the sensors included here. Any of these sensor(s) 180 can be located within the electronic device 101.

The first external electronic device 102 or the second external electronic device 104 may be a wearable device or an electronic device 101-mountable wearable device (such as a head mounted display (HMD)). When the electronic device 101 is mounted in an HMD (such as the electronic device 102), the electronic device 101 may detect the mounting in the HMD and operate in a virtual reality mode. When the electronic device 101 is mounted in the electronic device 102 (such as the HMD), the electronic device 101 may communicate with the electronic device 102 through the communication interface 170. The electronic device 101 may be directly connected with the electronic device 102 to communicate with the electronic device 102 without involving with a separate network.

The wireless communication may use at least one of, for example, long term evolution (LTE), long term evolution-advanced (LTE-A), code division multiple access (CDMA), wideband code division multiple access (WCDMA), universal mobile telecommunication system (UMTS), wireless broadband (WiBro), or global system for mobile communication (GSM), as a cellular communication protocol. The wired connection may include at least one of, for example, universal serial bus (USB), high definition multimedia interface (HDMI), recommended standard 232 (RS-232), or plain old telephone service (POTS). The network 162 may include at least one communication network, such as a computer network (like a local area network (LAN) or wide area network (WAN)), the Internet, or a telephone network.

The first and second external electronic devices 102 and 104 each may be a device of the same type or a different type from the electronic device 101. According to embodiments of this disclosure, the server 106 may include a group of one or more servers. Also, according to embodiments of this disclosure, all or some of the operations executed on the electronic device 101 may be executed on another or multiple other electronic devices (such as the electronic devices 102 and 104 or server 106). Further, according to embodiments of this disclosure, when the electronic device 101 should perform some function or service automatically or at a request, the electronic device 101, instead of executing the function or service on its own or additionally, may request another device (such as electronic devices 102 and 104 or server 106) to perform at least some functions associated therewith. The other electronic device (such as electronic devices 102 and 104 or server 106) may execute the requested functions or additional functions and transfer a result of the execution to the electronic device 101. The electronic device 101 may provide a requested function or service by processing the received result as it is or additionally. To that end, a cloud computing, distributed computing, or client-server computing technique may be used, for example.

While FIG. 1 shows that the electronic device 101 includes the communication interface 170 to communicate with the external electronic device 102 or 104 or server 106 via the network(s) 162 and 164, the electronic device 101 may be independently operated without a separate communication function, according to embodiments of this disclosure. Also, note that the electronic device 102 or 104 or the server 106 could be implemented using a bus, a processor, a memory, an I/O interface, a display, a communication interface, and an event processing module (or any suitable subset thereof) in the same or similar manner as shown for the electronic device 101.

Although FIG. 1 illustrates one example of a network configuration 100, various changes may be made to FIG. 1. For example, the network configuration 100 could include any number of each component in any suitable arrangement. In general, computing and communication systems come in a wide variety of configurations, and FIG. 1 does not limit the scope of this disclosure to any particular configuration. Also, while FIG. 1 illustrates one operational environment in which various features disclosed in this patent document can be used, these features could be used in any other suitable system.

Figure 2:
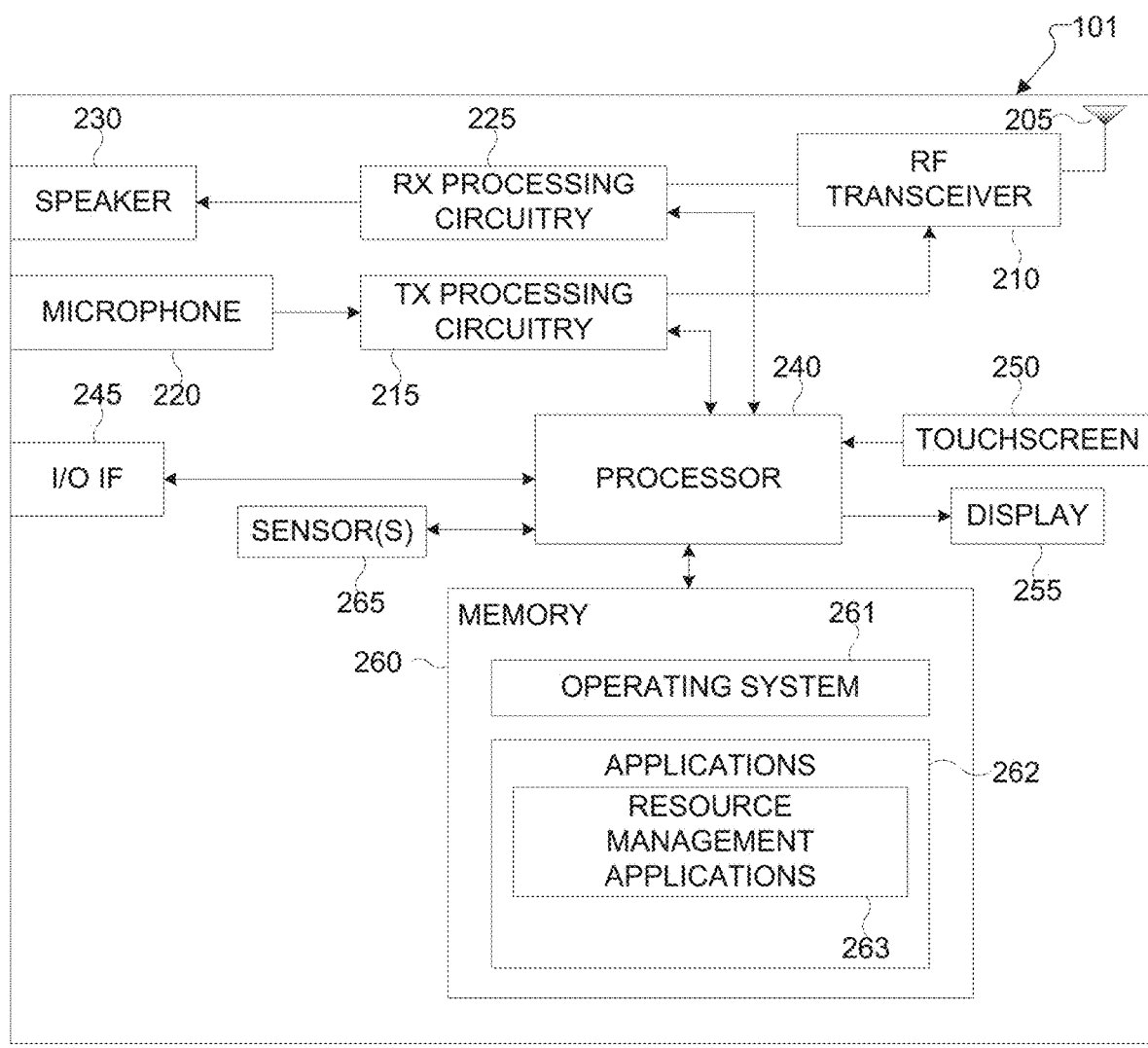
FIG. 2 illustrates an example electronic device in accordance with this disclosure.

FIG. 2 illustrates an example electronic device 101 in accordance with this disclosure. The electronic device 101 could represent one or more of the electronic devices 101, 102, or 104 in FIG. 1. As shown in FIG. 2, the electronic device 101 includes an antenna 205, a radio frequency (RF) transceiver 210, transmit (TX) processing circuitry 215, a microphone 220, and receive (RX) processing circuitry 225. The electronic device 101 also includes a speaker 230, a processor 240, an input/output (I/O) interface (IF) 245, an input 250, a display 255, and a memory 260. The memory 260 includes an operating system (OS) program 261 and one or more applications 262.

The RF transceiver 210 receives, from the antenna 205, an incoming RF signal transmitted by another component in a system. The RF transceiver 210 down-converts the incoming RF signal to generate an intermediate frequency (IF) or baseband signal. The IF or baseband signal is sent to the RX processing circuitry 225, which generates a processed baseband signal by filtering, decoding, and/or digitizing the baseband or IF signal. The RX processing circuitry 225 transmits the processed baseband signal to the speaker 230 (such as for voice data) or to the processor 240 for further processing (such as for web browsing data).

The TX processing circuitry 215 receives analog or digital voice data from the microphone 220 or other outgoing baseband data (such as web data, e-mail, or interactive video game data) from the processor 240. The TX processing circuitry 215 encodes, multiplexes, and/or digitizes the outgoing baseband data to generate a processed baseband or IF signal. The RF transceiver 210 receives the outgoing processed baseband or IF signal from the TX processing circuitry 215 and up-converts the baseband or IF signal to an RF signal that is transmitted via the antenna 205.

The processor 240 can include one or more processors or other processors and execute the OS program 261 stored in the memory 260 in order to control the overall operation of the electronic device 101. For example, the processor 240 could control the reception of forward channel signals and the transmission of reverse channel signals by the RF transceiver 210, the RX processing circuitry 225, and the TX processing circuitry 215 in accordance with well-known principles. In some embodiments, the processor 240 includes at least one microprocessor or microcontroller.

The processor 240 is also capable of executing other processes and programs resident in the memory 260. The processor 240 can move data into or out of the memory 260 as required by an executing process. In some embodiments, the processor 240 is configured to execute the applications 262 based on the OS program 261 or in response to signals received from external devices or an operator. The processor can execute a resource management application 263 for monitoring system resources. The processor 240 is also coupled to the I/O interface 245, which provides the electronic device 101 with the ability to connect to other devices such as laptop computers, handheld computers and other accessories, for example, a virtual reality (VR) headset. The I/O interface 245 is the communication path between these accessories and the processor 240. The processor 240 can recognize accessories that are attached through the I/O interface 245, such as a VR headset connected to a USB port.

The processor 240 is also coupled to the input 250 and the display 255. The operator of the electronic device 101 can use the input 250 (e.g., keypad, touchscreen, button etc.) to enter data into the electronic device 101. The display 255 may be an LCD, LED, OLED, AMOLED, MEMS, electronic paper, or other display capable of rendering text and/or at least limited graphics, such as from web sites.

The memory 260 is coupled to the processor 240. Part of the memory 260 could include a random access memory (RAM), and another part of the memory 260 could include a Flash memory or other read-only memory (ROM).

The electronic device 101 further includes one or more sensors 265 that can meter a physical quantity or detect an activation state of the electronic device 101 and convert metered or detected information into an electrical signal. For example, the sensor 265 may include any of the various sensors 180 discussed above.

Although FIG. 2 illustrates one example of an electronic device 101, various changes may be made to FIG. 2. For example, various components in FIG. 2 could be combined, further subdivided, or omitted and additional components could be added according to particular needs. As a particular example, the processor 240 could be divided into multiple processors, such as one or more central processing units (CPUs) and one or more graphics processing units (GPUs). Also, while FIG. 2 illustrates the electronic device 101 configured as a mobile telephone or smart phone, electronic devices could be configured to operate as other types of mobile or stationary devices. In addition, as with computing and communication networks, electronic devices can come in a wide variety of configurations and FIG. 2 does not limit this disclosure to any particular electronic device.

Figure 3:
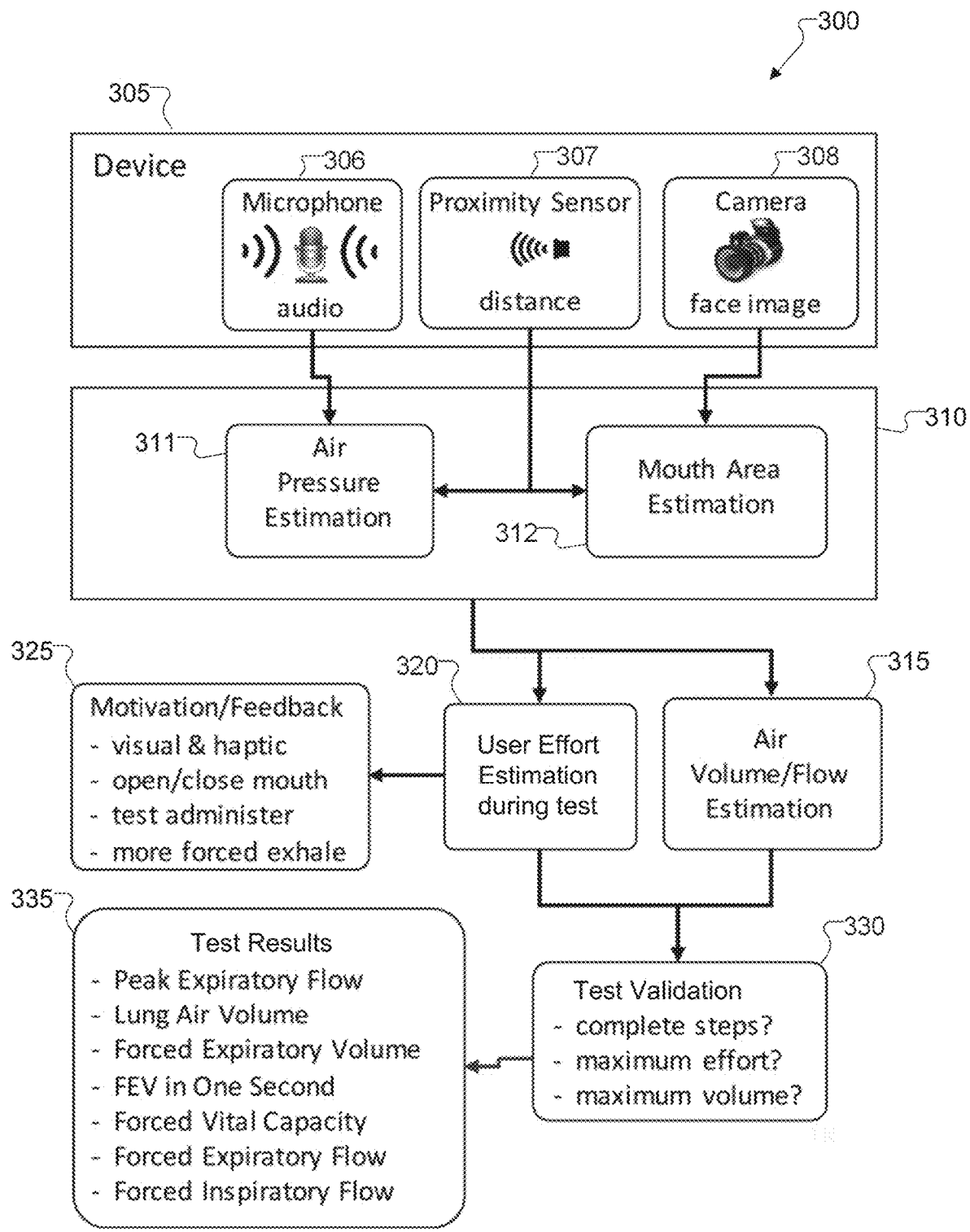
FIG. 3 illustrates an example system for performing an on-device spirometry test in accordance with this disclosure.

FIG. 3 illustrates an example system 300 for performing an on-device spirometry test in accordance with this disclosure. For ease of explanation, the system 300 is described as involving at least one electronic device (such as the electronic device 101 of FIG. 1). However, the system 300 could involve any other suitable device(s) or system(s) without departing from the scope of this disclosure.

As shown in FIG. 3, the system 300 includes a mobile device 305. The mobile device 305 is a mobile electronic device that is associated with (or used by) a user who may have a respiratory condition that can be monitored by a spirometry test. The mobile device 305 may represent one of the electronic devices 101, 102, 104 of FIG. 1. For example, the mobile device 305 may be the user's smart phone, smart watch, or tablet.

The mobile device 305 includes an audio sensor 306 that is capable of detecting and recording audio in the vicinity of the mobile device 305, such as the microphone 220 of FIG. 2. During the spirometry test, the audio sensor 306 can detect and record audio associated with the user breathing, including inhalation and exhalation. The mobile device 305 also includes a proximity sensor 307 that is capable of detecting and recording position and distance relative to another object. The proximity sensor 307 can represent, or be represented by, one or more of the sensors 180 of FIG. 1. During the spirometry test, the proximity sensor 307 can detect and measure a distance from the user's face or mouth to the mobile device 305. The mobile device 305 also includes an image sensor 308 that is capable of detecting and recording images and video, such as a front facing camera. During the spirometry test, the image sensor 308 can detect and record still or video images of the user's face or mouth. Although FIG. 3 illustrates only one of each of the sensors 306-308, other embodiments could include more than one of any or all of the sensors 306-308.

During the spirometry test, the mobile device 305 instructs the user to hold the mobile device in front of the user's face such that the image sensor 308 can detect the user's face. In some embodiments, a preferred distance between the user's face and the mobile device 305 is approximately fifteen centimeters, although the distance may vary during the test and shorter and longer distances are within the scope of this disclosure. The mobile device 305 instructs the user to inhale and exhale near the audio sensor 306. As with most spirometry tests, the test is most accurate when the user inhales deeply and then exhales quickly and completely. A typical spirometry test lasts approximately six seconds, although the time could be shorter or longer, depending on the user. As the user inhales and exhales, the audio sensor 306 captures the sound created by the air flow and pressure and converts the sound into sound data. Likewise, the proximity sensor 307 detects and determines the distance from the mobile device 305 to the user's face, and the image sensor 308 records still or video images of the user's face or mouth. Using the sound data, distance data, and image data obtained during the spirometry test, the mobile device performs multiple estimation functions 310, including an air pressure estimation function 311 and a mouth area estimation function 312.

Figure 4:
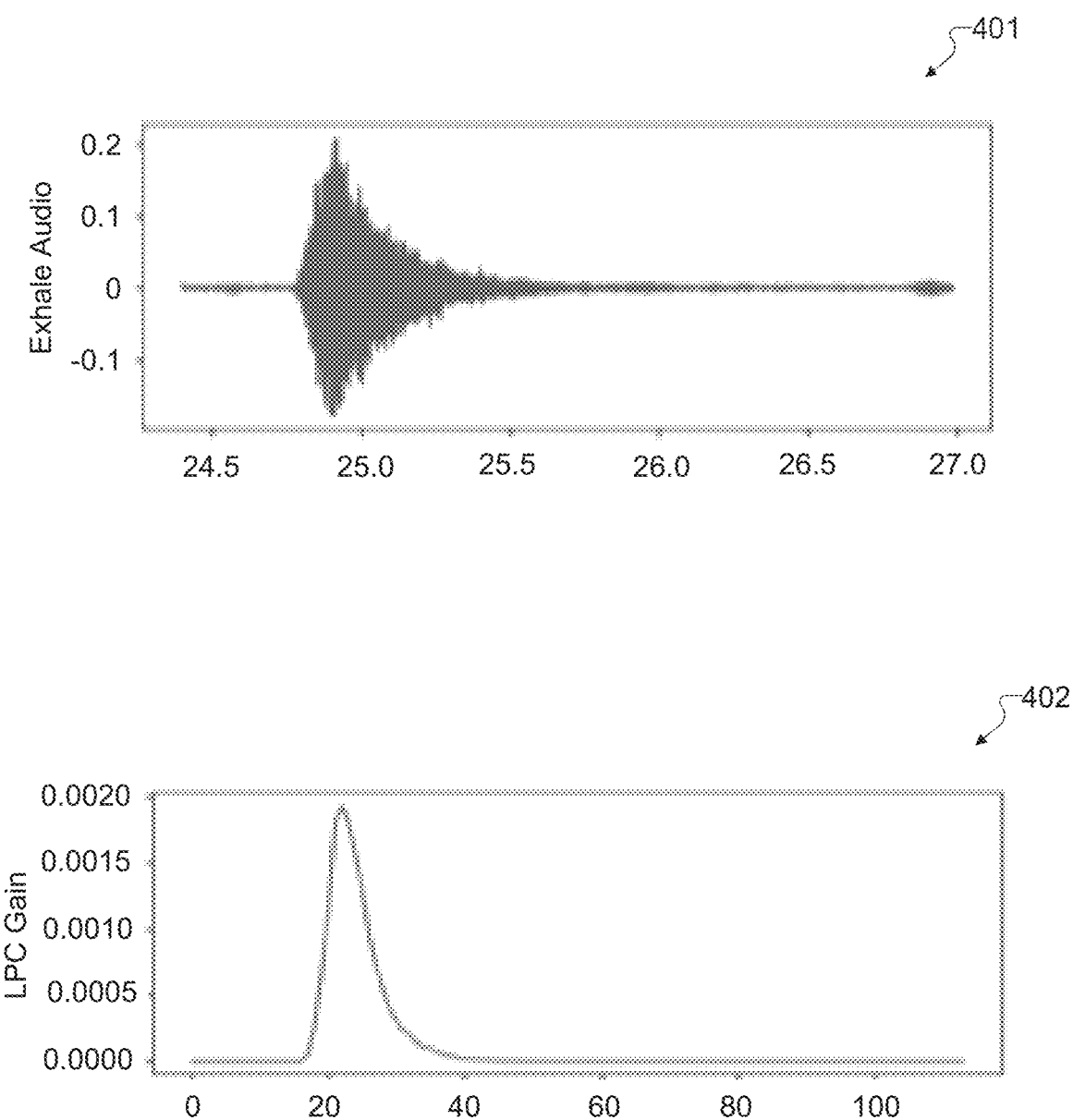
FIG. 4 illustrates an example plot of an air pressure curve and an example plot of Linear Predictive Coding (LPC) gain of audio obtained during the spirometry test in accordance with this disclosure.

In the air pressure estimation function 311, the mobile device 305 uses audio signal processing to detect and extract the inhalation and exhalation sections of the sound data and estimate the air pressure created during each section by analyzing the energy level and frequency features of the audio. In some embodiments, the mobile device 305 extracts information regarding air flow and air pressure by analyzing the Linear Predictive Coding (LPC) features of the audio during the inhalation and exhalation process. For example, FIG. 4 illustrates an example plot 401 of an air pressure curve and an example plot 402 of LPC gain of the audio obtained during a spirometry test in accordance with this disclosure. Since the LPC features extracted from the audio lie in the low-mid range of frequency spectrum, the LPC are quite reliable even when audio is captured behind the screen of the device. In some embodiments, estimation models can be pre-trained using recorded audio from different microphones located in various locations to improve the robustness of the estimation.

In some embodiments, the mobile device 305 can remove background noise by capturing and subtracting the sound profile of the environment. Moreover, the mobile device 305 can ignore noisy sound events (short term or long term) by considering a higher threshold in segmenting out the breathing events of inhalation and exhalation. It is expected that there may be variations in the audio data during different spirometry tests, considering different ways of blowing near the device. In certain embodiments, the mobile device 305 accounts for these variations and avoids the steps of distance/volume calibration by using other context data such as captured images of subject mouth/face and distance between face and device, as explained in greater detail below.

In the mouth area estimation function 312, the mobile device 305 uses the image data from the image sensor 308, the distance data from the proximity sensor 307, and one or more image processing techniques to estimate the area of the opening of the mouth while the user inhales and exhales during the spirometry test. The mobile device 305 uses the estimated area of the mouth in measuring the amount of air volume exchange. This is due to the fact that the area of the mouth while inhaling and exhaling influences the air pressure and thereby the amount of air volume exchange. Furthermore, mouth area data constitutes personalized data of each user while conducting the test. This feature enables the mobile device 305 to account for subject-to-subject variations. Therefore, mouth shape calibration or subject training before the spirometry test can be avoided while improving the accuracy of the results. This is important for an accurate measurement since there may be no medical supervision of the user while the user conducts the test.

Estimation of a shape in an image and estimation of the area of that shape has intrinsic error due to the challenges of image processing. For instance, the area of the mouth could be calculated differently depending on the distance of the face from the front camera. Therefore, the mobile device 305 considers the estimated distance between the user's face and the device 305 in the mouth area estimation function 312 to compensate for this possibility.

The mobile device 305 can use any of several possible techniques for distance estimation. For example, as discussed above, the mobile device 305 can use distance data from the proximity sensor 307. In some embodiments, mobile device 305 could additionally or alternatively use data from a personal image profile. In such a profile, a pre-obtained baseline image of the user's face at a fixed distance would be established as the reference point for estimating the mouth area and distance from the device. In some embodiments, the mobile device 305 could use data from one or more internal motion sensors to measure the geometric distance between the mobile device 305 and the user's mouth by identifying the upper-arm length, position and orientation of the mobile device 305 with respect to a body coordinate system centered at the shoulder of the user. The distance can be estimated while moving the mobile device 305 from face or pocket to the requested location facing the user's face. As another example, depth-field cameras may provide the distance information of the user's face in the camera image. As yet another example, a mechanical aid, such as a string or band, between the user and the mobile device 305 can be used to maintain a constant distance between the user's face and the mobile device 305

It is noted that, in some embodiments of the spirometry test, the user may place the user's mouth around a mouth piece during inhalation and exhalation. In such an embodiment, the cross-sectional area of the mouth piece may be known by the mobile device 305, in which case, estimation of the mouth area would not be needed.

After the mobile device 305 has estimated the air pressure and mouth area during the spirometry test, the mobile device 305 performs an air volume/flow estimation function 315 to measure the amount of air volume exchange during exhalation and inhalation. The air volume exchange is measured by estimating the air flow in and out of the mouth. That is, the mobile device 305 uses one or more of the recorded audio, the mouth/face image data, and the distance from the user's face to the mobile device 305 to estimate the amount of air volume exchange during the spirometry test. In some embodiments, the air volume exchange can be empirically inferred from features of the captured audio and image data or by training a regression or machine learning model that captures the relationship. The mobile device 305 tracks the amount of air volume exchange for the whole duration of the spirometry test. The mobile device 305 can accurately estimate the amount of air volume exchange without the need for complicated device calibration by the user.

The mobile device 305 estimates the amount of air volume exchange, which is directly correlated with the air flow and pressure and the mouth opening area, as shown in the following, given the assumption that the user's effort is at its maximum (i.e., the user's air flow during the spirometry test is at or close to the maximum amount possible by the user):

$$Q[\text{air volume exchange}] = v[\text{air flow}] \times A[\text{mouth area}] \quad (1)$$

where, e.g., Q can have units of liters/second, v can have units of meters/second, and A can have units of $cm^2$.

After estimating the amount of air volume exchange during the test, the mobile device 305 also determines one or more pulmonary function parameters, such as Peak Expiratory Flow (PEF), Maximal Expiratory Flow (MEF), Forced Expiratory Volume (FEV), FEV in One Second (FEV1), Forced Vital Capacity (FVC), Forced Expiratory Flow (FEF), and Forced Inspiratory Flow (FIF). These parameters represent the lung health of the user and should be in a certain range considering the user's lung condition.

Figure 5:
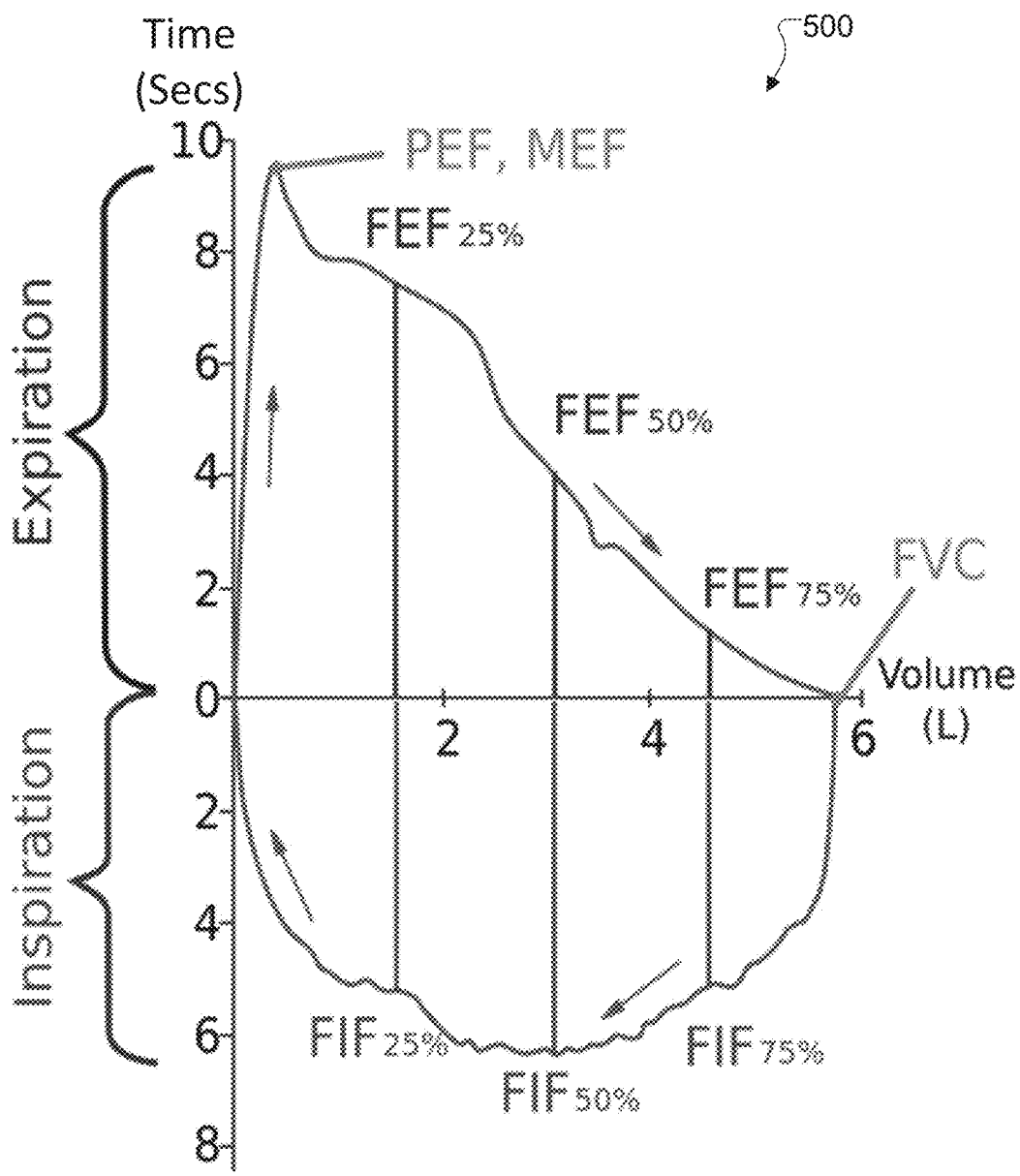
FIG. 5 illustrates an example air flow/volume curve with multiple pulmonary function parameters evaluated after a complete spirometry test in accordance with this disclosure.

FIG. 5 illustrates an example air flow/volume curve 500 with multiple pulmonary function parameters indicated after a complete spirometry test in accordance with this disclosure. The mobile device 305 processes the curve 500 and the temporal data to extract the pulmonary function parameters, which indicate the user's pulmonary health condition. The mobile device 305 can use any suitable techniques or algorithms to determine each of the pulmonary function parameters. The values for the pulmonary function parameters can be compared with statistics and normal values in order to provide a higher-level summary to the user in terms of the user's overall lung health. For instance, the value of the FEV1/FVC ratio can be used to classify the user's lung health into different severity levels (e.g., mild, moderate, and severe).

After the mobile device 305 has estimated the air pressure and mouth area during the spirometry test, the mobile device 305 also performs a user effort estimation function 320 to determine the amount of effort by the user during the spirometry test. In particular, the mobile device 305 uses the air pressure and face features estimated during the inhalation and exhalation process to determine the amount of effort that the user put into the test, map to the user's stress level, and compare to the user's maximum baseline. The mobile device 305 uses the amount of the user's effort estimated over time to provide feedback and, e.g., guide the user to adjust the way the user conducts the test or motivate the user to accomplish a correct test.

A common challenge of conventional spirometry solutions is the difficulty of having the subject perform the spirometry test correctly. For maximum success, the subject is required to fully inhale, and then forcefully exhale into the device with their highest effort. Failure to do these steps correctly can result in decreased accuracy. In a medical setting, a trained clinician or pulmonologist may be available to guide the subject through the test. The clinician or pulmonologist may ask the subject to retry the test multiple times in order to get their best effort. In in-home or other portable spirometry tests, medical personnel may not be available and the effort of the subject is not evaluated. Thus, the subject is not properly notified of the subject's lack of effort during the test. Moreover, current solutions for in-home spirometry consider rule-based techniques which do not properly represent the effort of subjects and they may fail to provide accurate test results.

In contrast, in the system 300, the mobile device 305 uses the recorded audio, the mouth/face image of the user, the distance from the user's face to the mobile device 305, or a combination of these, in order to quantify the effort put into inhalation and exhalation by the user. The mobile device 305 continuously measures the effort by the user during the spirometry test to ensure maximum effort throughout the test. In some embodiments, the mobile device 305 estimates the probability that the user is completely filling up his or her lung capacity when inhaling and emptying it out when exhaling, thus resulting in maximum air volume exchange. In addition, the mobile device 305 estimates the probability that the user is using maximum force while exhaling, resulting in the maximum air flow and pressure. The mobile device 305 then uses these metrics to quantize the user effort, and guide or motivate the user to increase the user's effort or adjust the user's technique in performing the test. In general, user effort can be demonstrated in the following factors:

Facial Features: The location, shape, or color of the subject's mouth, jaw, or eyes may change depending on the amount of effort put into inhalation and exhalation. It has been shown that blowing effort and the stress of the test can influence the blood perfusion and face skin color depending on the pressure put on the subject.

Recorded Audio: The energy, duration, or frequency features of the recorded audio would be affected depending on the effort put into exhalation and inhalation. This is due to the fact that the forced muscle activation would change the size of the vocal cords and tubes resulting in different resonances, which can be demonstrated in change of audio frequency features.

Stress Level: It has been shown that the stress level can be passively measured by a photoplethysmogram (PPG) sensor, which is an included component of some mobile devices. Therefore, the self-reported effort values and stress level activity can be used as potential ground truths and target values in training the user effort estimation models.

Based on some or all of these factors, the mobile device 305 can perform the user effort estimation function 320 to determine a level of user effort while the user performs the spirometry test. For example, using machine learning techniques, the mobile device 305 maps the facial features and audio features and their changes during the test to one or more quantity metrics indicating the user's effort. This effort can be compared to the user's baseline, and the comparison can be used to ensure that the user maintains maximum effort throughout the test. The quantity metrics represent the percentage and probability of maximum possible air volume exchange and maximum possible air flow. These mappings can be captured empirically or by training a regression or machine learning model, as indicated by the formulas below.

$$f_{train}(\text{stress level}, \text{effort}) \to P[\text{max air vol exchange}] \sim f(x_{face\ shape}, x_{recorded\ audio}) \quad (2)$$

$$f_{train}(\text{stress level}, \text{effort}) \to P[\text{max air flow}] \sim f(x_{face\ shape}, x_{recorded\ audio}) \quad (3)$$

Based on the amount of user effort estimated in the user effort estimation function 320, the mobile device 305 may provide real-time feedback 325 to the user during or after the spirometry test. Typically, in medical settings, subjects are trained before a spirometry test or they are motivated by clinicians during the test to ensure their maximum effort is put into the test. However, medical supervision is usually not possible for portable spirometry. To address this, the mobile device 305 provides the real-time feedback 325 to guide the user to adjust a behavior to maximize or improve the user's effort and possibly prevent multiple attempts of the spirometry test. The approaches used to provide the feedback 325 to the user can vary depending on the scenario, user, and motivation of the feedback. For example, the feedback 325 provided by the mobile device 305 can include one or more of the following:

Visual Feedback: The mobile device 305 can show messages or instructions, such as "Exhale!", on the display of the mobile device 305 to instruct or guide the user while performing the test. In some embodiments, the mobile device 305 can provide augmented reality (AR) visual feedback on the front camera image that guides the user to: 1) open/close their mouth further, or 2) get closer to or farther from the device. This can include graphical indicators, such as arrows, superimposed on the camera image of the user's mouth. Other visual feedback can include interactive motion graphics that motivate the user to increase and continue their effort during the test, if low effort has been detected. For instance, the user can be encouraged to increase the user's air flow force.

Haptic Feedback: The mobile device 305 can use haptic feedback (e.g., use of vibrations) to notify and guide the user to continue his or her effort during the test and to stop the test. In some embodiments, the intensity or duty cycle of the vibration can indicate the user's effort and support the user during the test as a motivating component.

Audio Feedback: The mobile device 305 can generate one or more sounds (e.g., beeps, buzzes, rings, spoken language sounds, and the like) to notify the user of any error or to encourage the user during the spirometry test. For example, a pulsing sound can be used to give feedback on the intensity of the effort made by the user.

After the mobile device 305 has estimated the air volume exchange and the amount of user effort, the mobile device 305 performs a test validation function 330 to determine if the spirometry test was completed correctly. In general, spirometry tests are typically accurate, unless the subject did not properly conduct the test. In medical settings, any mistakes are typically noticed by a clinician. However, for in-home spirometry, the challenge would be to identify the mistakes by looking at only the measurements. Conventional in-home spirometry solutions consider rule-based techniques that monitor the curve of the air flow during the test. However, they may fail in validation of the test and identifying any mistakes, as the air flow curve does not fully represent the way the subject performed the test; instead, the air flow curve is an output of the test, which may be affected by personal health condition or test imperfection.

To address this, the mobile device 305 performs the test validation function 330 to determine if the spirometry test was completed correctly or if any mistakes were made by the user during the test. In particular, the test validation function 330 utilizes one or more of recorded audio, mouth/face images, or distance from face to device during the test to validate the test and identify any mistakes made by the user during exhalation or inhalation. In the test validation function 330, the mobile device 305 compares the quantified user effort curve over the time of the test to the air flow volume curve. These features should correlate and match each other, and at the same time should validate the following criteria in order to ensure a complete and correct spirometry test:

Acceptable position of device against face/mouth during the test.

Acceptable pattern of inhalation and forced exhalation.

Maximum effort by the user throughout the test.

Sensible air volume exchange during the test (intake volume>=exhale volume).

If any of the above criteria are not correct, this can be indicative of a mistake performed by the user during the test. The mobile device 305 performs the test validation function 330 to identify the type and time of any mistakes made by the user. Mistakes can include, e.g., early termination of the test, lack of effort by the user at any time during the test, inconsistent air flow, air volume mismatch (i.e., the amount of air exhaled by the user is not the same as the amount of air inhaled), and the like.

In some embodiments, the test validation function 330 includes an anomaly detection algorithm for each of the above criteria to identify the mistakes and amount of misalignment. In some embodiments, the test validation function 330 generates an overall score to represent the amount of correctness and completeness of the test. This score is estimated using the above-mentioned features and criteria extracted from the recorded data. The mobile device 305 can map the score from these features to a scalar value by training a regression or machine learning model. In some embodiments, the criteria and variables that had a significant influence on the value drop of the score are identified as the mistakes during the test. The mobile device 305 can provide the results of the test validation function 330 to the user as feedback, including any identified mistakes, so that the user can adapt their way of conducting the test.

In addition to reporting the results of the test validation function 330, the mobile device 305 also reports test results 335 to the user. The test results 335 can include the user effort curve over the time of the test, the air flow volume curve, the amount of air volume exchange, one or more of the pulmonary function parameters (PEF, MEF, FEV, FEV1, FVC, FEF, FIF), or any combination of these. In some embodiments, the values of the pulmonary function parameters can be compared with statistics and normal values in order to provide a higher-level summary to the user as an indicator of the user's overall lung health. For instance, the value of the FEV1/FVC ratio can be used to classify the user's lung health into different severity levels (e.g., mild, moderate, and severe).

The mobile device 305 can show the test results 335 on the display of the mobile device 305, or the mobile device 305 can send the test results 335 to another device (e.g., a medical clinic server) for evaluation by a medical professional. The test results 335 can be used by the user or the medical professional for diagnostic or treatment purposes. In some embodiments, the test results 335 can improve treatment or make treatment more efficient by providing more frequent, more accurate spirometry information. For example, the test results 335 could reveal a breathing condition that, if observed early, would result in less significant medical treatment (e.g., less medication), but if not diagnosed until later, might result in asthma attack or exacerbation that would require more significant treatment (e.g., more medication or even surgery), admission to an emergency room, or hospitalization.

Although FIG. 3 illustrates one example of a system 300 for performing an on-device spirometry test, various changes may be made to FIG. 3. For example, the system 300 could be implemented in any suitable manner, such as entirely within the mobile device 305 or using a combination of devices. As a particular example, at least some of the functions and operations can be implemented or supported using one or more software applications or other software instructions that are executed by one or more processor(s) 120, 240 of the mobile device 305. In other embodiments, at least some of the functions and operations can be implemented or supported using dedicated hardware components. In general, the functions and operations can be performed using any suitable hardware or any suitable combination of hardware and software/firmware instructions. In some embodiments, the mobile device 305 could collect the audio, image, and proximity data and provide the data to a server 106, which could then perform some of the operations of FIG. 3. Results of the processing could then be made available to the mobile device 305 and/or one or more other devices (such as the electronic device 102 or 104). In general, computing and communication systems come in a wide variety of configurations, and FIG. 3 does not limit the scope of this disclosure to any particular configuration.

Other possible changes to FIG. 3 include one or more of the following, which are within the scope of this disclosure.

In a case where one or more wearable devices include the sensors 306-308, the spirometry test can be conducted exclusively on the wearable devices by holding the wearable devices facing the user and blowing into them. The various data collection and processing functions of the system 300 would be the same or similar on the wearable devices as on the mobile device 305. In some embodiments, the mobile device 305 and a wearable device could complement each other in the spirometry test. For example, sensor data from both the mobile device 305 and the wearable device can be collected together and time synchronized, such that the fused sensor data is used for evaluating the results. As a particular example, a smart phone can be held with the hand that is wearing a smart watch when the spirometry test is conducted. The audio, image, or sensory data (for distance) collected from both devices would complement each other, and may improve the accuracy of the results.

In some embodiments, the amount of air volume exchange can be estimated in various ways using alternative methods. For example, one or more motion sensors of the mobile device 305 or a wearable device can be used to measure the user's chest movements when conducting the spirometry test. The chest movements can be used to estimate air volume exchange and later mapped to the pulmonary function parameters and air volume. As another example, one or more contactless sensors (e.g., infrared sensor, thermal imaging sensor, etc.) or other cameras can estimate lung parameters when the user is performing the spirometry test in front of the sensors. A heatmap or images generated by these sensors can be used to measure the chest movements when conducting the test. The chest movements can be used to estimate air volume exchange and later mapped to the pulmonary function parameters.

In some embodiments, image and audio data can be captured using a device other than the mobile device 305 or a wearable device. For example, an external camera placed in proximity to the user can record audio or image data of the user conducting the test. The external camera can then send the data to the mobile device 305 so that the mobile device 305 can process the data and evaluate the results. As another example, video and audio recorded through other software technologies, such as a video chat tool, can be used for evaluating results.

In some embodiments, when the user performs the spirometry test on a mobile device, it can be important or necessary to identify the forced exhalation in the continuous mobile sensor data before the lung function biomarkers, such as FEV1, FVC, FEV1/FVC, PEF, or the like, are estimated. The presence of the forced exhalation can be estimated in continuous mobile sensor time series data using a template-based algorithm described below or using one or more machine learning algorithms such as Random Forest, Logistic Regression, XGBoost, Support Vector Machine, or the like, by performing left out validation.

In some embodiments, how hard the user forces his or her exhalation can greatly affect the reliability of the lung function biomarker measurement. Therefore, it is advantageous to estimate the quality of the effort captured by mobile sensor data. In some embodiments, the detection and effort quality assessment can be performed together or in succession. In one embodiment, a window of 6-second audio is detected as a forced exhalation segment. The start of the exhalation can be further pinpointed by removing the initial silence based on an empirically learned energy threshold. It is noted that the audio of the forced exhalation is mostly audible in the first 2-3 seconds out of a 6 second effort. Therefore, the Time To Peak Flow (TTPF) is an quality parameter for mobile spirometry. From observing the distribution of the TTPF analysis from a training dataset, it is noted that the high quality efforts' TTPF may go up to 400 milliseconds. If the TTPF is more than 400 milliseconds, it is considered a poor effort and may be discarded from the assessment.

To ensure that high quality efforts are detected and appropriate feedback is provided to the user who is using the smartphone spirometry at home without any clinician supervision, the system 300 can further analyze the shape of the envelope of a forced expiratory effort sound. In some embodiments, a shape based time series data modeling approach is used to detect a template of the forced exhalation sounds from the rigorously annotated sound segments. A percentile based approach to generate an individual envelope performs better than traditional approaches, such as maximum value or root mean square (RMS) based approaches. The system 300 can compute the mean of the individual envelopes from the training data to generate the template envelope for high fidelity forced expiratory effort sounds.

The similarity between the template and the individual envelope can be used as a metric for mobile spirometry. The similarity can be computed as the absolute distance between the template (which is the expected shape) and the envelope from individual forced expiratory sound segments as described in the equations below. First, the construction of the template is described as:

$$T[n] = \frac{1}{K}\sum_{k=1}^{K} Env_k[n], \quad \forall\, n \in [1, n]$$

where T[n] is the nth sample of the envelope template T, $Env_k$ [n] is the nth sample of the kth envelope $Env_k$ in the training set, K is the total number of envelopes that have an available sample at the nth position, and N is the total number of samples in the longest envelope. The distance metric is then computed as the absolute difference between each of the data points of the current envelope $Env_c$ and the template envelope T as the equation given below:

$$D = \sum_{i=1}^{M} \|Env_c[i] - T[i]\|$$

where M is the total number of samples in the current envelope $Env_c$, and it is assumed that M<=N, where N is the total number of samples in the template T.

Figure 6:
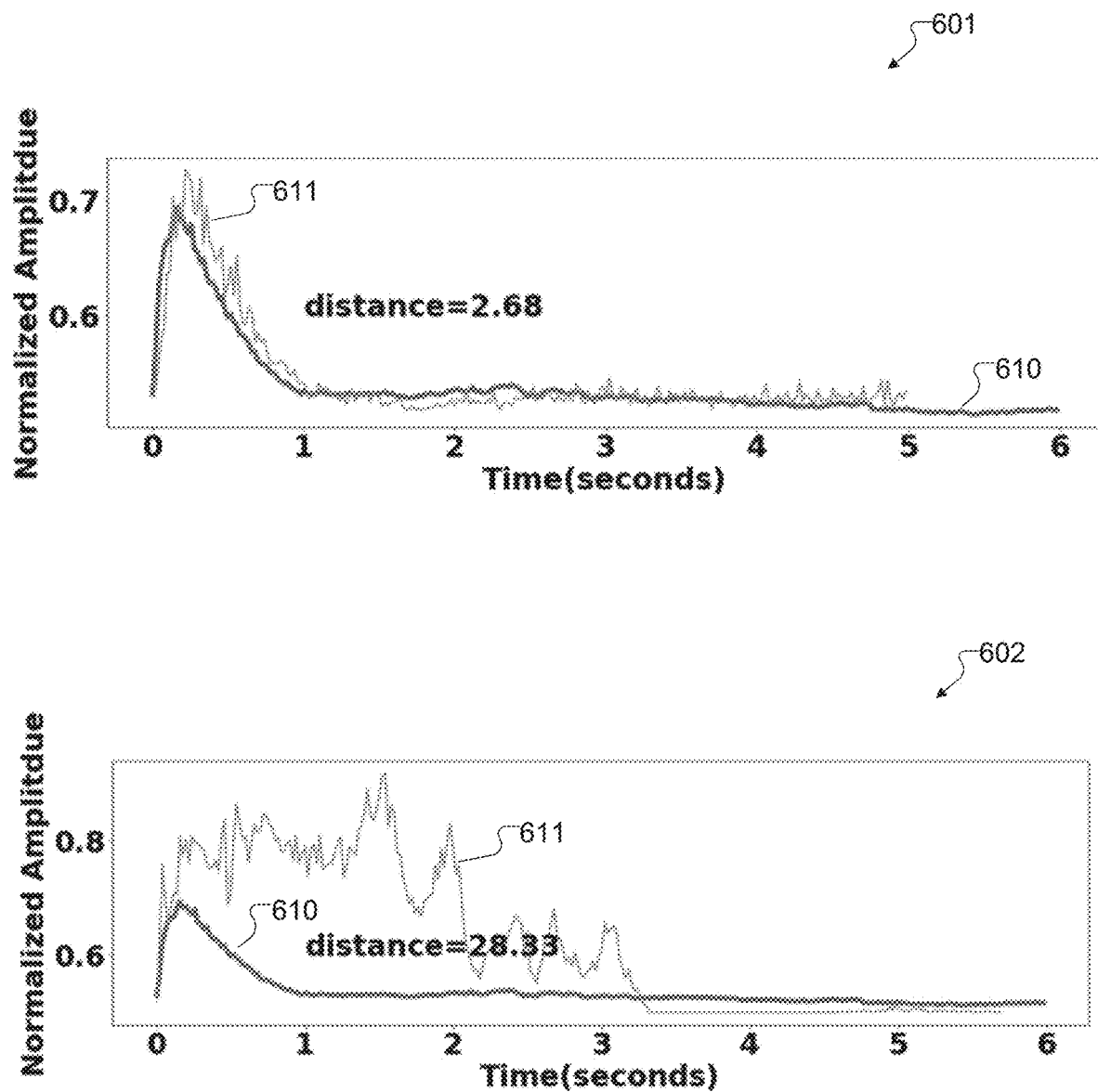
FIG. 6 illustrates two plots showing a similarity between a template and a current forced exhalation from a spirometry test in accordance with this disclosure.

FIG. 6 illustrates two plots 601-602 showing a similarity between the template and the current forced exhalation from a spirometry test in accordance with this disclosure. From the dataset, the similarity metric is computed for all the smartphone spirometry efforts, and the distribution of the distance is plotted.

As shown in FIG. 6, the distance from the template can help identify the expected effort from a poor effort. The plot 601 shows low distance and high similarity, while the plot 602 show high distance and low similarity. In each plot 601-602, the curve 610 represents the template envelope and the curve 611 represent the current effort under investigation. It can be observed that the higher the distance, the lower the quality of the effort. It can also be observed that a similarity distance more than a certain threshold can divide the high quality efforts from the poor efforts. Other embodiments can use other important features such as correlation, variance, mean, with the distance metric to train a machine learning model to identify high quality effort from the poor efforts. The user interface can provide the guidance based on the detected effort quality to the user to try again to produce a reliable lung function measurement.

Figure 7:
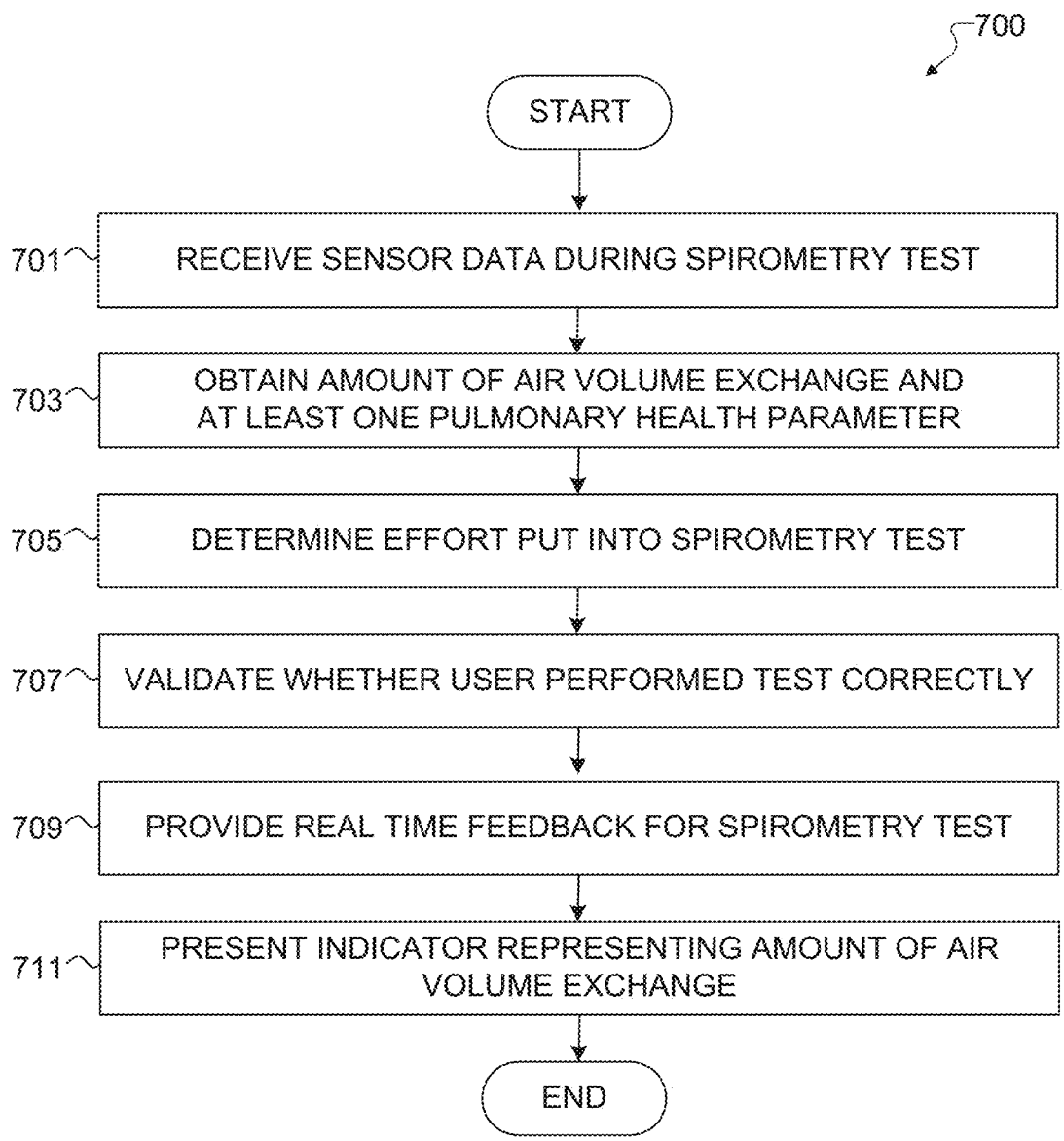
FIG. 7 illustrates an example method for performing an on-device spirometry test in accordance with this disclosure.

FIG. 7 illustrates an example method 700 for performing an on-device spirometry test in accordance with this disclosure. For ease of explanation, the method 700 shown in FIG. 7 is described as involving the use of the mobile device 305 of FIG. 3. However, the method 700 shown in FIG. 7 could be used with any other suitable electronic device and in any suitable system.

At operation 701, the mobile device 305 receives sensor data during a spirometry test of a user. The sensor data includes audio data of the user and distance data of a distance from a face of the user to the mobile device 305. This can include, for example, the mobile device 305 receiving audio data from the audio sensor 306 and receiving distance data from the proximity sensor 307. In some embodiments, the sensor data further includes image data of the face of the user. The image data can be received from the image sensor 308.

At operation 703, the mobile device 305 obtains an amount of air volume exchange and at least one pulmonary health parameter that are determined based on the audio data and the distance data. In some embodiments, the amount of air volume exchange and the at least one pulmonary health parameter are further determined based on the image data. This can include, for example, the mobile device 305 determining the amount of air volume exchange and the at least one pulmonary health parameter by performing the air volume/flow estimation function 315. Alternatively, this can include the mobile device 305 receiving the amount of air volume exchange and/or at least one pulmonary health parameter from another device, such as the server 106, after the other device determines the amount of air volume exchange and the at least one pulmonary health parameter.

At operation 705, the mobile device 305 determines an amount of effort put into the spirometry test by the user based on at least one of the audio data, the image data, and the distance. This can include, for example, the mobile device 305 performing the user effort estimation function 320 to determine the amount of effort put into the spirometry test by the user.

At operation 707, the mobile device 305 validates whether the user performed the spirometry test correctly. This can include, for example, the mobile device 305 performing the test validation function 330 to determine whether the user performed the spirometry test correctly.

At operation 709, the mobile device 305 provides real time feedback after validating that the user did not perform the spirometry test correctly. This can include, for example, the mobile device 305 providing visual feedback, audio feedback, haptic feedback, or any combination of these, to the user. The feedback can identify any mistakes performed by the user during the test and provide corrective actions for the user to take.

At operation 711, the mobile device 305 presents an indicator on a display of the mobile device 305 for use by the user or a medical provider, where the indicator represents the amount of air volume exchange. This can include, for example, the mobile device 305 presenting one or more of the test results 335 on the display of the mobile device 305. The test results 335 can include the user effort curve over the time of the test, the air flow volume curve, the amount of air volume exchange, one or more of the pulmonary function parameters (PEF, MEF, FEV, FEV1, FVC, FEF, FIF), or any combination of these.

Although FIG. 7 illustrates one example of a method 700 for performing an on-device spirometry test, various changes can be made to FIG. 7. For example, various steps in FIG. 7 could overlap, occur in parallel, occur serially, occur in a different order, or occur any number of times. Also, various steps could be removed and/or other steps could be added. In addition, the steps of the method 700 could be implemented in any suitable manner, such as entirely within the mobile device 305 or using a combination of devices. For instance, as indicated above, the mobile device 305 could collect data and provide the data to a server 106, which could then process the data and generate any suitable output.

Some smart devices (e.g., the mobile device 305) may be equipped with more than one channel for audio recording using multiple microphones disposed at different locations in or on the device. Using such devices, some embodiments include capturing the forced exhalation audio in a stereo mode. That is, the forced exhalation events can be captured by more than one channel. For example, when a user performs the spirometry test at home without any clinical supervision, the user may hold the device comfortably close to the user's mouth and blow the user's maximum exhalation into the device. It is noted that there can be different ways for the user to hold the device, e.g., horizontally, vertically, or tilted at an angle. Therefore, due to variations in orientation of the device with respect to the user's mouth, one channel (e.g., one microphone) may capture better sound than another channel (e.g., another microphone); the direction of the blowing with respect to the location of the microphones can influence the audio and its energy features.

Figure 8:
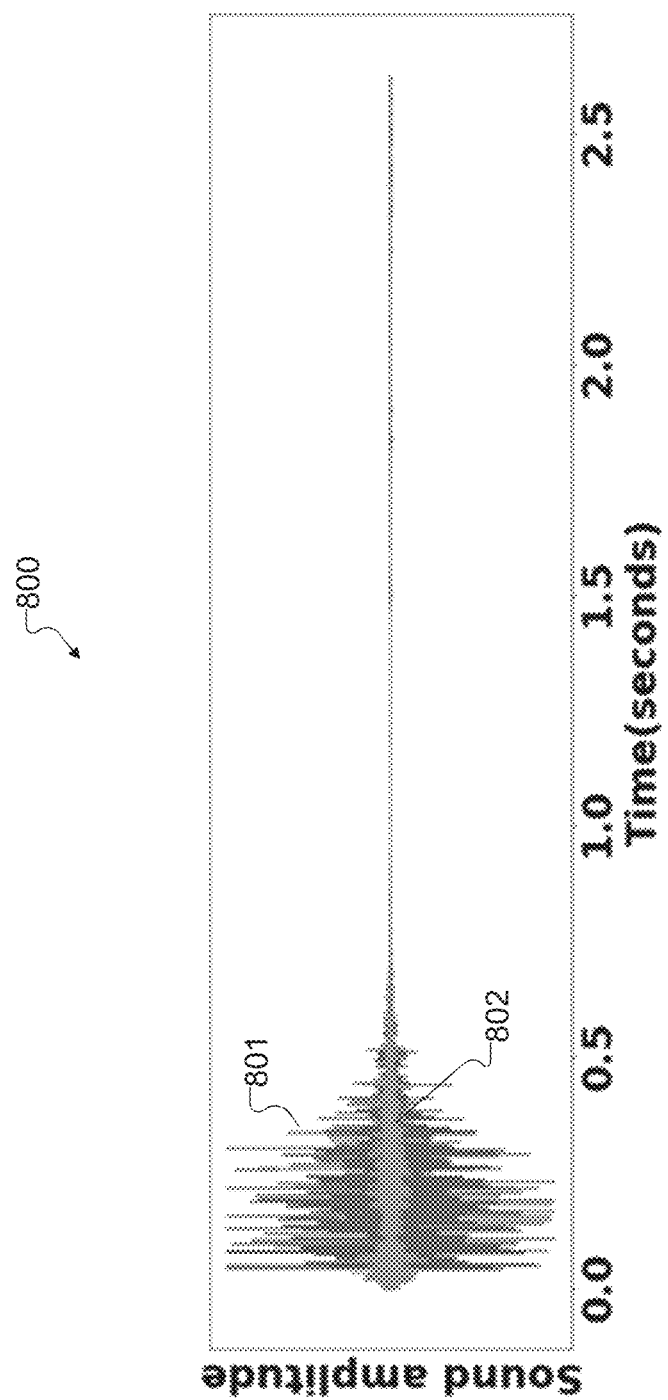
FIG. 8 illustrates an example plot of sound amplitude of a user exhalation captured over time using multiple channels in accordance with this disclosure.

FIG. 8 illustrates an example plot 800 of sound amplitude of a user exhalation captured over time using multiple channels in accordance with this disclosure. The embodiment of the plot 800 of sound amplitude of a user exhalation shown in FIG. 8 is for illustration only and other example plots, different data values, different orientations, or different scenarios could be used without departing from the scope of the present disclosure.

In the example shown in FIG. 8, the curve 801 shows the sound amplitude of the user exhalation as captured using a first channel, and the curve 802 shows the sound amplitude of the user exhalation as captured using a second channel. The plot 800 shows that, even though the same forced exhale sound is captured by both channels, due to differences in orientation, one channel captures the sound better than the other. Moreover, the intensity of the audio sensed by a smart device microphone can also vary due to variation in distance between the mouth and the smart device.

In some embodiments in which multiple channels can capture exhalation audio, one or more of the channels can be selected for audio processing using one or more channel selection algorithms. The channel selection algorithm can make the selection based on the sound intensity, the sound envelope, other sound characteristics or parameters, or a combination of these. In some embodiments, sensor data from one or more sensors (e.g., an inertial measurement unit (IMU)) provide orientation information of the smart device. The orientation information and audio data from multiple channels can be used to identify the best channel for the analysis. The channels can be sorted based on a reliability score correlated with the audio envelope, energy, signal-to-noise ratio, orientation of the smart device, or a combination of these. Audio from the channel with the highest reliability score can be selected for analysis. In certain embodiments, the signals from all the available channels are fused to provide the audio for analysis. The fusion is achieved by assigning weights to the channels and combining the weighted signal information together (e.g., using a summation operation or another suitable mathematical or analysis operation). The weights can be defined based on the audio envelope, energy, signal-to-noise ratio, orientation information of the smart device, or a combination of these.

In some embodiments, the channel selection algorithm can monitor sensor data (e.g., from an IMU sensor or another suitable sensor) to evaluate the angle and orientation of the smart device when performing spirometry. The position and orientation of the smart device can influence the quality of the audio captured from each microphone and channel. For example, consider a smart phone that has a primary microphone disposed near the bottom of the smart phone, and one or more other microphones disposed elsewhere on the smart phone. When the user is holding the smart phone horizontally with the bottom microphone in front the user's mouth, higher-quality audio is captured from the bottom microphone channel compared to other channels. Alternatively, when the user holds the smart phone in another orientation (e.g., with the bottom microphone away from the user's mouth), another microphone (closer to the user's mouth) may capture higher intensity audio, while the bottom microphone may capture higher fidelity (but lower intensity) audio. Therefore, based on the orientation of the phone, and with knowledge of where each microphone and channel are located, the channel selection algorithm adjusts the weights given to each channel when selecting one channel or evaluating the fused (combined) audio for processing, to ensure high quality audio capture. The distance and location of the device with respect to the user can be measured using the IMU sensor or other sensor, which enables the channel selection algorithm to further adjust and determine the weights given to each channel.

In a scenario of using a foldable device, such as SAMSUNG GALAXY Z FLIP, the fold angle formed by partial folding of the device can be used as an additional feature to determine the best channel for audio collection. For example, the fold angle information can be used to further determine which microphone or channel is closer to the user's mouth whether the device is in a flat orientation or is folded at 90 degrees or another angle.

In some embodiments, the smart device can monitor the audio envelope, energy, signal-to-noise ratio, or a combination of these, to determine the higher-quality channel when capturing the spirometry audio. This data can be used instead of (or in addition to) the phone orientation and distance information to adjust the weights given to each channel. This approach enables the channel selection algorithm to select the best channel when the device orientation or distance does not provide sufficient information regarding the best channel. For example, when a smart phone is positioned vertically, two microphones, disposed in the bottom and top of the phone respectively, may capture similar audio quality; however, the direction of the user's mouth can influence which microphone (i.e., channel) captures better-quality audio. In this scenario, the features extracted from the audio (e.g., audio energy, envelope, SNR, and the like) are utilized to adjust the weights when selecting a channel or creating the fused audio signal for processing. In some embodiments, the channel selection algorithm can include a machine learning or rule-based model that uses these features to decide which channel is the best option, or to assign weights to each channel. The model and the parameters can be determined empirically or by training using pre-recorded audio data from all channels. For instance, the best quality audio is expected to have the highest audio energy, envelope with the largest area-under-curve, or highest SNR. Of course, the determination of best quality audio is not limited thereto; other determinations are within the scope of this disclosure.

As discussed above, in order to promote a successful pulmonary function test, the user is typically instructed to fully inhale, and then forcefully exhale into the device with their highest effort. Failure to perform these steps correctly can result in incorrect or inaccurate measurements. Typically, supervision from clinicians and multiple attempts would increase the chance of having the maximum effort; however, when conducting PFT at home, the user may not have any supervision, and may be less compliant. Therefore, in some embodiments, the smart device may be configured to estimate the effort of the user and guide the user to maintain effort as high as possible during the spirometry session.

The spirometry effort is mainly demonstrated in the process of inhalation and exhalation of the spirometry. The user behavior and amount of air exchanged during the spirometry test are influenced by this effort. In some embodiments, features from audio data are used to measure or estimate the user's effort. Examples of such features can include energy, duration, and frequency features. The spirometry effort can be quantified in terms of the probability of the audio features matching and correlating with audio features from a predetermined maximum-effort spirometry session audio. The audio features would be affected by the effort the user puts in exhalation and inhalation. The forced activation of user muscles to generate maximum effort changes the size of the vocal cords and tubes, resulting in different resonances that are reflected in different audio frequency features. A machine learning or rule-based model can use these features to determine the spirometry effort from the user. The model and the parameters can be trained using pre-recorded audio as explained below. Additionally or alternatively, historical baseline data from the user can be used to adjust the estimation of the spirometry effort.

As an illustrative example, a study was performed in which training data was collected from more than 210 patients. In the study, several mobile spirometry audio samples were collected from each subject. One goal of the study was to learn a template of a high-quality effort from the audio envelope of the forced exhalation that is consistent across different subjects. The study included two major components—(i) detect spirometry effort in a continuous audio timeseries data, and (ii) estimate the envelope of the spirometry effort audio.

In the study, the presence of the forced exhalation was detected in each window using machine learning classification algorithms. Among the detected exhalations, the annotated forced exhalation examples were considered to be positive examples. Other common pulmonary sounds, such as coughs, deep inhalations, regular breathing sounds, 'Aaa . . . ' vowel sounds, other ambient noises (e.g., silence), and the like, were considered to be negative examples. The model was built using 210 positive examples and 3953 negative examples. To reduce the skewness of the data, the negative class was downsampled such that it included a similar number of samples; however, representative samples from each negative category were maintained. The dataset was split into train (80%) and validation sets (20%). A ten-fold cross validation technique was used on the train dataset, and a Random Forest ensemble classifier was used to detect a forced exhalation event. Finally, the model performance was tested using a left-out validation dataset.

After detection of a window of six-second audio as a forced exhalation segment, the start of the exhalation was determined by removing the initial silence based on an empirically learned energy threshold. It can be observed that the forced exhalation is mostly audible in the first 2-3 seconds of the six second effort. Therefore, the traditional quality model of the American Thoracic Society (ATS) and European Respiratory Society (ERS) may not work during such a test. Instead, the parameters from the ATS/ERS guidelines that are more relevant for the mobile spirometry were determined and their thresholds were modified. For example, time-to-peak-flow (TTPF) was set to 400 milliseconds (ms). If a spirometry effort's TTPF <400 ms, it was considered to be a poor effort and was discarded from the assessment.

Figure 9:
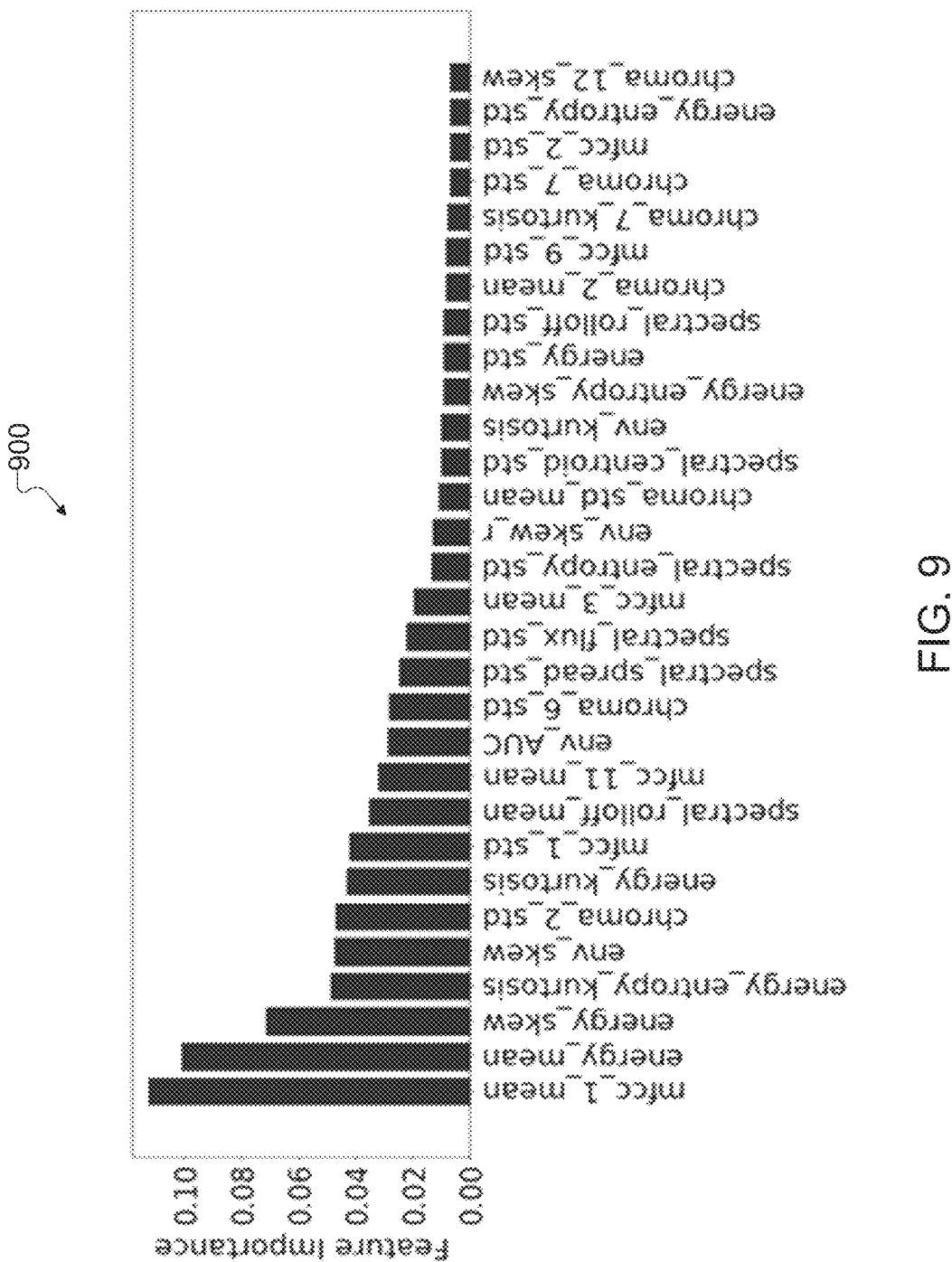
FIG. 9 illustrates an example chart showing importance of different features for determining mobile spirometry effort in accordance with this disclosure.

Using a Random Forest classifier, an F1-score of 96.74%±1.84% was achieved in the study. Multiple features for determining the spirometry effort were determined and ordered by importance. For example, FIG. 9 illustrates an example chart 900 showing importance of different features for determining mobile spirometry effort in accordance with this disclosure. The chart 900 and underlying data is for illustration only and other data sets and representations could be used without departing from the scope of the present disclosure.

As shown in the chart 900, it was determined that the mean of first Mel frequency cepstral coefficient (MFCC), mean energy, skewness of energy, kurtosis of energy entropy, skewness of envelope, and standard deviation of the second chroma feature can be the six most important features in identifying a forced exhalation from other sounds in an audio timeseries data. It is noted that MFCC represents a spectral envelope of a sound signal. The energy features of the forced exhalation effort sound, the spectral envelope feature, and the percentile envelope features have more discriminatory power to identify a smart device spirometry event.

In some embodiments, features from a user's face are used to measure and estimate the user effort. In these embodiments, the spirometry effort is quantified in terms of the percentage of changes in the facial features when correlating with changes in facial features from a maximum-effort spirometry session audio. Facial features such as position or shape of the mouth/jaw/cheeks, color of skin, and size of eye can change depending on the amount of effort put in the inhalation and exhalation. For example, a user's cheeks will often expand further with higher effort during exhalation. Also, the user's eyes may become wider and bigger as they put more effort in the test. In addition, blowing effort and the stress of the test may influence the blood perfusion and change the user's face skin color more towards a red or purple color.

Using machine learning techniques, on top of the audio features explained previously, the smart device can map the additional data from facial features and their changes during the test to a quantity metric of the user's effort. This effort can be compared to the user's baseline and used to ensure that the user maintains their maximum effort throughout the test. These metrics represent the percentage and probability of maximum possible air volume exchange and maximum possible air flow.

In some embodiments, the smart device monitors user stress level and uses the stress level to quantify the user's effort during the spirometry session. For example, the stress level can be passively measured by a PPG sensor on the smart device (if available). During the test, the smart device can evaluate the stress level and monitor its change over time to determine the user effort.

The self-reported effort values and stress level activity can be also used as ground truths and target values in training the subject effort estimation models. The audio data and facial features from the training data can be correlated with the stress level from the subjects as an indication of subject effort. The mapping can be trained using a regression or machine learning model, which can be used to estimate stress level, and thereby subject effort, as indicated by the formulas in Equations (2) and (3) above.

In some embodiments, the smart device can measure spirometry effort using multiple features from audio data, facial expressions, stress level, and the like. Different priorities and weights can be assigned to each of the features, where each priority or weight correlates to an availability, accuracy, or reliability of the sensor data. For example, in some scenarios, stress level measurement may not be available, or portions of the user's facial features may be missed because the user's face is not captured properly. For instance, in a smart phone device, depending upon the location of the camera (e.g., the device is positioned too close or too far relative to the user's face), a portion of the user's face can be missed. In such a scenario, the captured distance information can be used to determine the reliability of the facial features. In another scenario, the fold angle between the two displays in a foldable smart phone can be used to identify how much of the face can be captured during spirometry. Therefore, in a case in which one or more portions of the features are missing, the smart device can apply a higher priority or weight in the subject effort estimation to audio features, which may be available and more reliable. Conversely, when the audio data does not provide reliable features to evaluate subject effort with high certainty because of noise or lack of energy, the smart device can apply a higher priority or weight to facial features and/or stress level. In the embodiment, the weights and priorities are used to aggregate the decisions derived from the multiple sources of sensory data.

Figure 10:
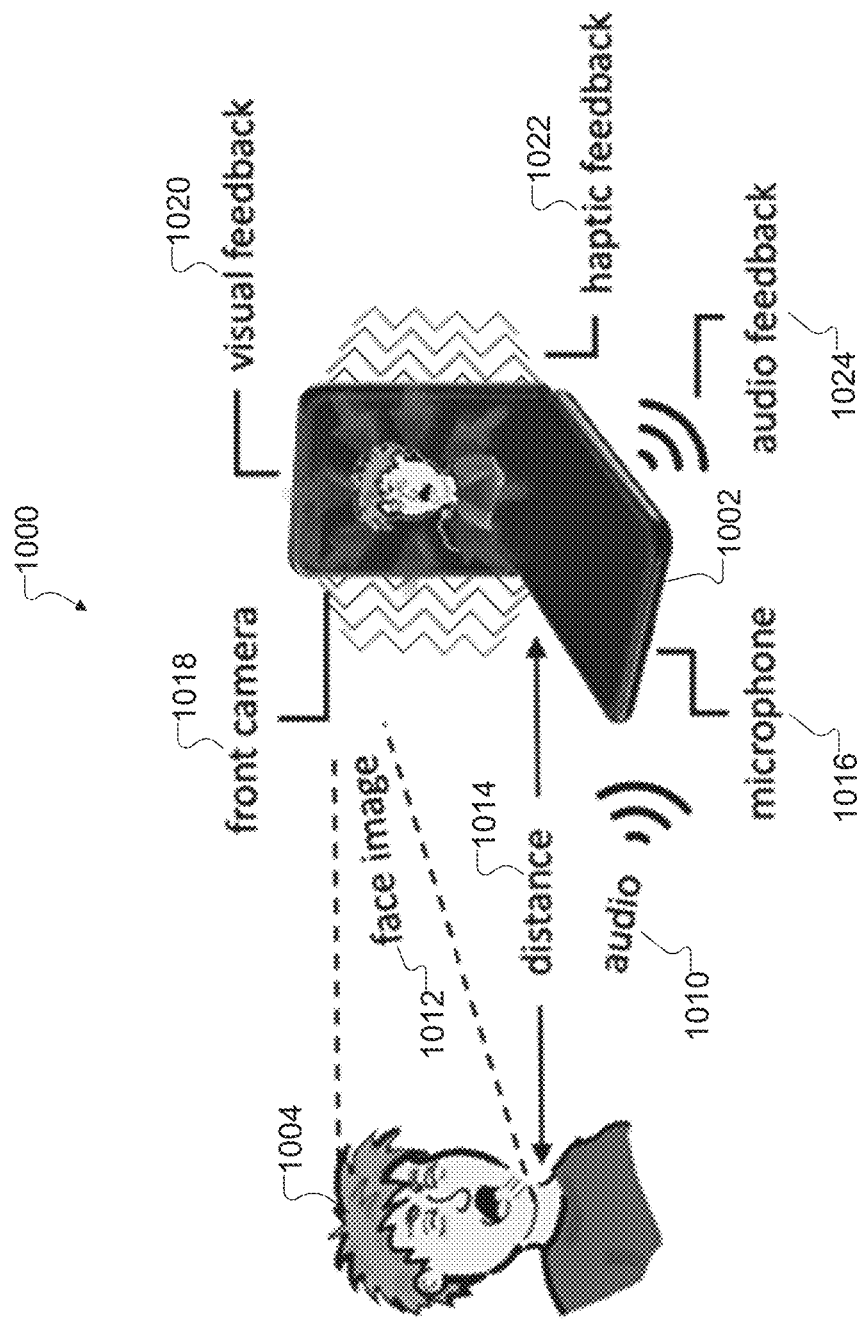
FIGS. 10 through 14 illustrate example systems for performing an on-device spirometry test using different smart devices in accordance with this disclosure.

FIG. 10 illustrates an example system 1000 for performing an on-device spirometry test using a foldable device, in accordance with this disclosure. For ease of explanation, the system 1000 is described as involving at least one electronic device (such as the electronic device 101 of FIG. 1). However, the system 1000 could involve any other suitable device(s) or system(s) without departing from the scope of this disclosure.

As shown in FIG. 10, the system 1000 includes a foldable device 1002, such as the SAMSUNG GALAXY Z FLIP. The foldable device 1002 may represent one of the electronic devices 101, 102, 104 of FIG. 1. The foldable device 1002 is configured to conduct mobile spirometry by capturing and analyzing information associated with a user 1004, such as audio 1010 generated by the user 1004, a face image 1012 of the user 1004, and a face-to-phone distance 1014.

The foldable device 1002 measures air volume exchange during inhalation and exhalation of the user 1004 by analyzing the audio 1010 through a microphone 1016 in the bottom of the foldable device 1002 while considering the face-to-phone distance 1014, which may represent a distance from the mouth or face of the user 1004 to the foldable device 1002. In some embodiments, the foldable device 1002 can include multiple microphones 1016 and multiple channels for recording audio. In such cases, the foldable device 1002 can perform a channel selection algorithm (such as described above) to identify the channel with the most reliable audio for analysis. The face-to-phone distance 1014 can be measured via a proximity sensor (similar to the proximity sensor 307 of FIG. 3), one or more motion sensors, by analyzing the face image 1012, using a depth camera, or using a combination of these. The foldable device 1002 can further analyze the amount of air volume exchange during the spirometry session to calculate one or more pulmonary function test parameters such as PEF, FEV1, FVC, and the like.

The foldable device 1002 further captures the face image 1012 and mouth structure of the user 1004 via a front camera 1018 when the foldable device 1002 is folded at an angle, such as a 90° angle. The features extracted from the face and mouth of the user 1004 are used to estimate the user's mouth area and adjust the air volume exchange during the spirometry session accordingly. In this embodiment, the position of the front camera 1018 and microphone 1016 when the foldable device 1002 is folded at an angle provides a convenient method for simultaneously collecting the user's audio, image, and distance data when the user 1004 conducts the spirometry test. Those of skill in the art will appreciate that the overall orientation of the foldable device 1002 relative to the user 1004 and the selected fold angle of the foldable device 1002 can affect the user's audio, image, and distance data relative to each other.

The foldable device 1002 further utilizes the face image 1012 and audio 1010 to estimate and measure the effort exerted by the user 1004 throughout the test. A value corresponding to the effort of the user 1004 can be determined and is an indication of how hard the user 1004 tries to deeply inhale, exhale quickly, and empty their lungs. The foldable device 1002 can monitor the value in order to provide real-time feedback to the user 1004 in case the user 1004 needs to try harder or adjust their spirometry test. The real-time feedback can help to ensure high compliance rate and reliable data collection for in-home testing (or at other locations where clinical supervision is lacking). The feedback provided to the user 1004 can include visual feedback 1020 using the front-facing display (folded at an angle), haptic feedback 1022 by increasing vibration intensity when higher effort is required, audio feedback 1024 to encourage higher effort from the subject, or a combination of these. The visual feedback 1020 can also include augmented reality (AR) feedback for guiding the user to adjust their mouth shape during the test, e.g., displaying arrows to indicate whether to widen or narrow the mouth.

The foldable device 1002 can analyze the data continuously collected from the user 1004 to validate the pulmonary function test and to identify any mistakes encountered during the test. The audio 1010, face image 1012, and distance data 1014 can be processed to determine which criteria for a valid test is met or identify when and what type of mistakes have occurred. This feature provides valuable feedback to the user 1004 to revise their effort quickly and reduce the number of attempts.

Figure 11:
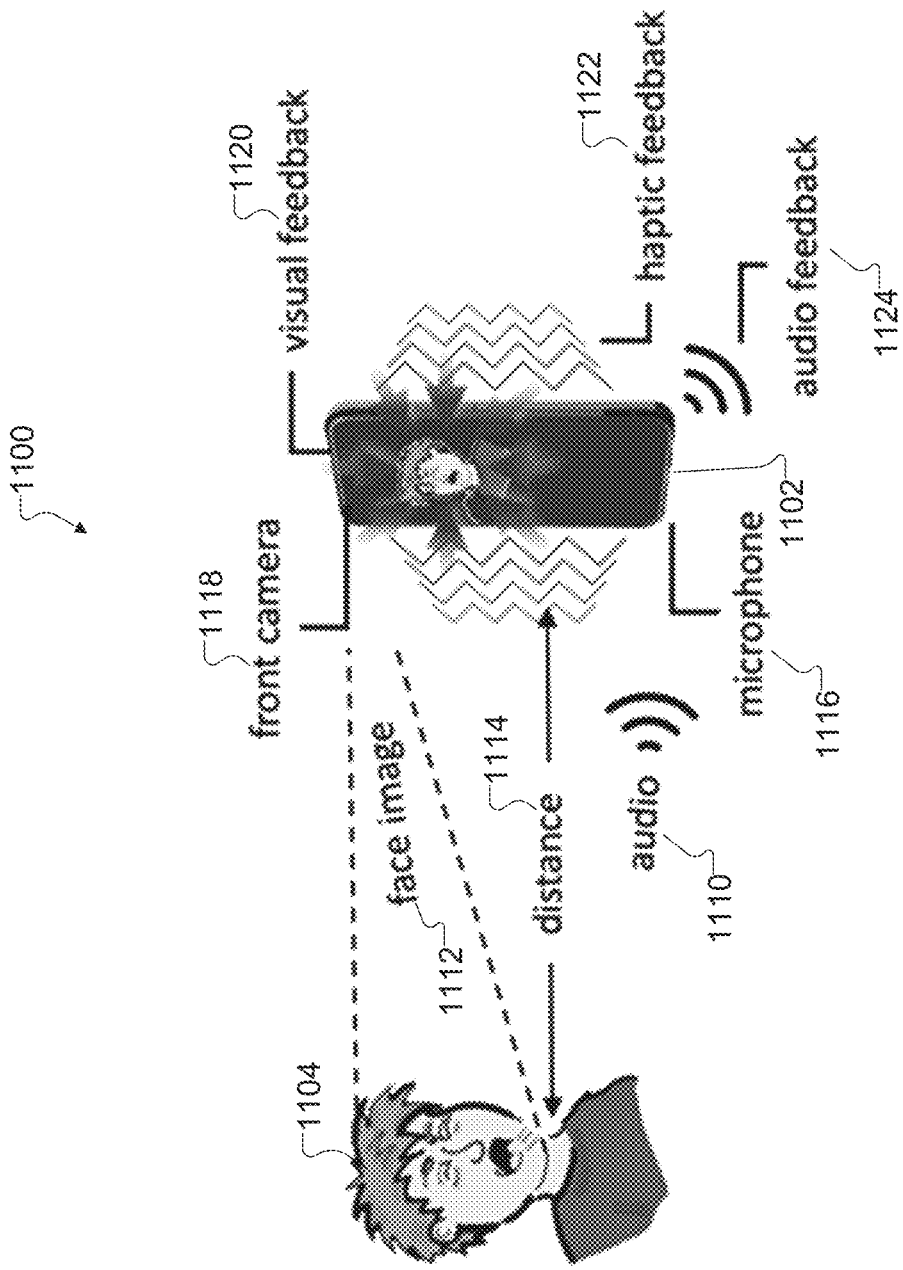

FIG. 11 illustrates an example system 1100 for performing an on-device spirometry test using a smart phone, in accordance with this disclosure. For ease of explanation, the system 1100 is described as involving at least one electronic device (such as the electronic device 101 of FIG. 1). However, the system 1100 could involve any other suitable device(s) or system(s) without departing from the scope of this disclosure.

As shown in FIG. 11, the system 1100 includes a smart phone 1102. The smart phone 1102 may represent one of the electronic devices 101, 102, 104 of FIG. 1. Similar to the foldable device 1002 of FIG. 10, the smart phone 1102 is configured to conduct mobile spirometry by capturing and analyzing information associated with a user 1104, such as audio 1110 generated by the user 1104, a face image 1112 of the user 1104, and a face-to-phone distance 1114.

The user 1104 conducts a pulmonary function test at home (or at another non-clinical location) using the smart phone 1102. To perform the test, the user 1104 holds the smart phone 1102 approximately 5-15 inches from the user's mouth facing the front camera 1118, then inhales and exhales into a microphone 1116 located at the bottom of the smart phone 1102. The smart phone 1102 measures air volume exchange during inhalation and exhalation of the user 1104 by analyzing the audio 1110 through the microphone 1116. In some embodiments, the smart phone 1102 can include multiple microphones 1116 and multiple channels for recording audio. In such cases, the smart phone 1102 can perform a channel selection algorithm (such as described above) to identify the channel with the most reliable audio for analysis. The face-to-phone distance 1114 can be measured via a proximity sensor (similar to the proximity sensor 307 of FIG. 3), one or more motion sensors, by analyzing the face image 1112, using a depth camera, or using a combination of these. The smart phone 1102 can further analyze the amount of air volume exchange during the spirometry session to calculate one or more pulmonary function test parameters such as PEF, FEV1, FVC, and the like.

During the test, the smart phone 1102 can provide real-time feedback to guide the user 1104 to adjust the test, correct their effort, or to avoid mistakes. The smart phone 1102 can measure the effort of the user 1104 during the test using the user's audio 1110 and face image 1112. The smart phone 1102 can provide real-time feedback to the user 1104 in case the user 1104 needs to try harder or adjust their spirometry test. The feedback provided to the user 1104 can include visual feedback 1120 provided on the front display while the user 1104 is inhaling and exhaling. The visual feedback 1120 can include AR arrows that can indicate how much the user 1104 should widen or narrow their mouth during inhalation or exhalation for a proper test. Haptic feedback 1122 or audio feedback 1124 can be provided during the test to motivate the user 1104 to increase their effort by blowing more quickly or fully emptying their lungs. After the test is finished and validated, the results of the pulmonary function test are provided on the display of the smart phone 1102 as numerical values or demonstrated in a chart. The smart phone 1102 can utilize the user's data during the test to identify mistakes made by the user 1104. The mistakes can be displayed as warnings so that the user 1104 can correct their effort for later attempts. The user 1104 can regularly take the test on the smart phone 1102 in a convenient location, and clinicians can remotely track the results and the user's lung function to monitor their recovery or worsening of symptoms.

Figure 12:
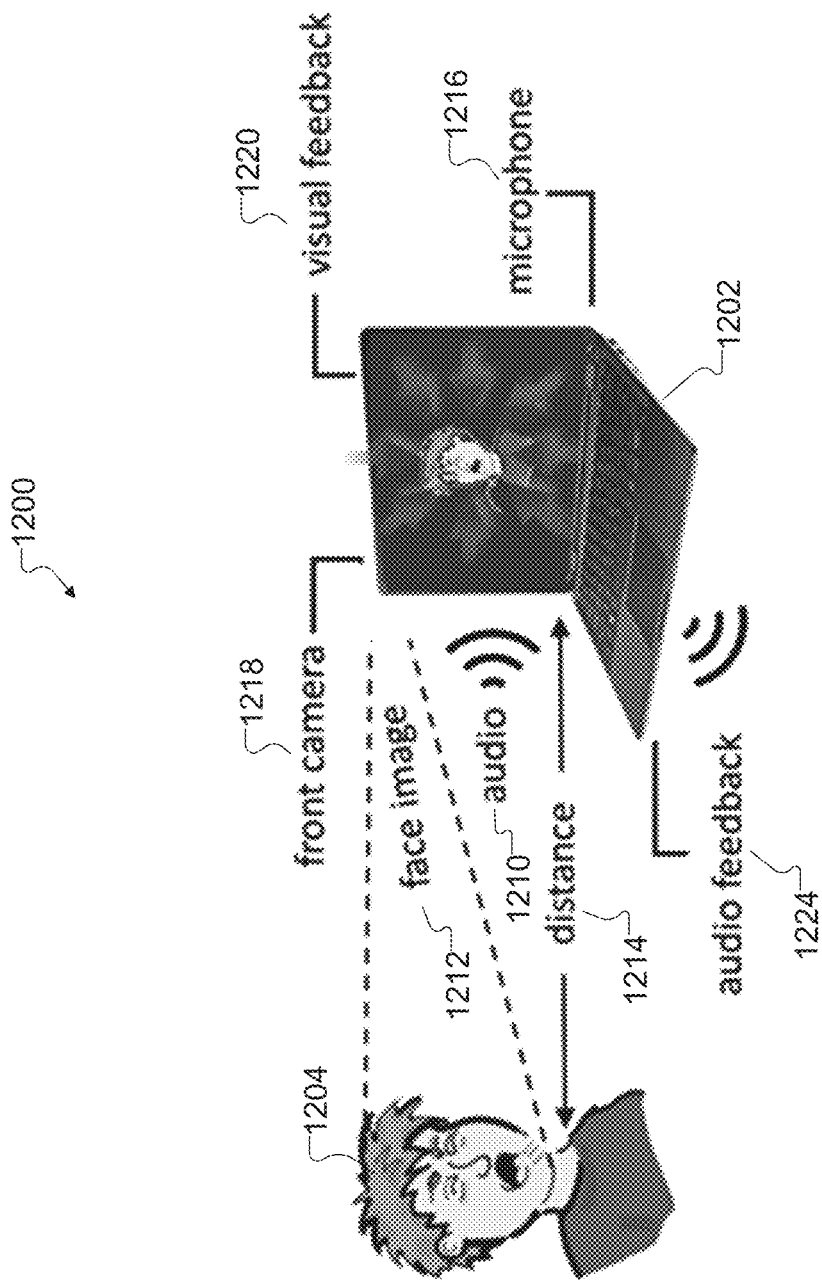

FIG. 12 illustrates an example system 1200 for performing an on-device spirometry test using a laptop computer, in accordance with this disclosure. For ease of explanation, the system 1200 is described as involving at least one electronic device (such as the electronic device 101 of FIG. 1). However, the system 1200 could involve any other suitable device(s) or system(s) without departing from the scope of this disclosure.

As shown in FIG. 12, the system 1200 includes a laptop computer (or simply "laptop") 1202. The laptop 1202 may represent one of the electronic devices 101, 102, 104 of FIG. 1. Similar to the foldable device 1002 of FIG. 10, the laptop 1202 is configured to conduct mobile spirometry by capturing and analyzing information associated with a user 1204, such as audio 1210 generated by the user 1204, a face image 1212 of the user 1204, and a face-to-laptop distance 1214.

The user 1204 conducts a pulmonary function test at home (or at another non-clinical location) using the laptop 1202. To perform the test, the user 1204 places the laptop 1202 on a surface approximately 5-15 inches from the user's mouth facing the front camera 1218, then inhales and exhales into a microphone 1216 located at the front of the laptop 1202. The laptop 1202 measures air volume exchange during inhalation and exhalation of the user 1204 by analyzing the audio 1210 through the microphone 1216. In some embodiments, the laptop 1202 can include multiple microphones 1216 and multiple channels for recording audio. In such cases, the laptop 1202 can perform a channel selection algorithm (such as described above) to identify the channel with the most reliable audio for analysis. The face-to-laptop distance 1214 can be measured via a proximity sensor (similar to the proximity sensor 307 of FIG. 3), one or more motion sensors, by analyzing the face image 1212, using a depth camera, or using a combination of these. The laptop 1202 can further analyze the amount of air volume exchange during the spirometry session to calculate one or more pulmonary function test parameters such as PEF, FEV1, FVC, and the like.

During the test, the laptop 1202 can provide real-time feedback to guide the user 1204 to adjust the test, correct their effort, or to avoid mistakes. The laptop 1202 can measure the effort of the user 1204 during the test using the user's audio 1210 and face image 1212. The laptop 1202 can provide real-time feedback to the user 1204 in case the user 1204 needs to try harder or adjust their spirometry test. The feedback provided to the user 1204 can include visual feedback 1220 provided on the display while the user 1204 is inhaling and exhaling. The visual feedback 1220 can include AR arrows that can indicate how much the user 1204 should widen or narrow their mouth during inhalation or exhalation for a proper test. Audio feedback 1224 can be provided during the test to motivate the user 1204 to increase their effort by blowing more quickly or fully emptying their lungs. After the test is finished and validated, the results of the pulmonary function test are provided on the display of the laptop 1202 as numerical values or demonstrated in a chart. The laptop 1202 can utilizes the user's data during the test to identify mistakes made by the user 1204. The mistakes can be displayed as warnings so that the user 1204 can correct their effort for later attempts. The user 1204 can regularly take the test on the laptop 1202 in a convenient location, and clinicians can remotely track the results and the user's lung function to monitor their recovery or worsening of symptoms.

Figure 13:
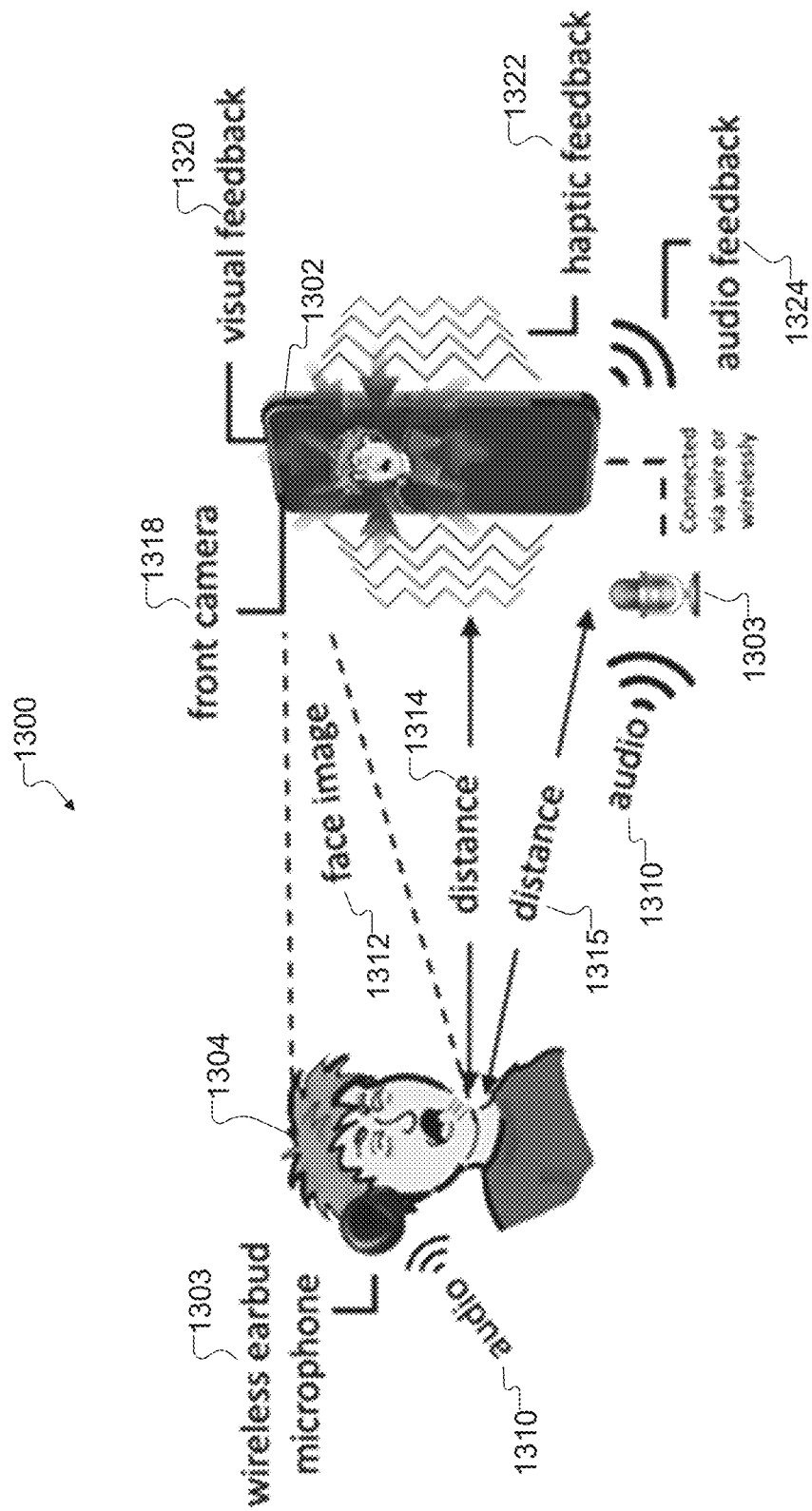

FIG. 13 illustrates an example system 1300 for performing an on-device spirometry test using a smart phone, in accordance with this disclosure. For ease of explanation, the system 1300 is described as involving at least one electronic device (such as the electronic device 101 of FIG. 1). However, the system 1300 could involve any other suitable device(s) or system(s) without departing from the scope of this disclosure.

As shown in FIG. 13, the system 1300 includes a smart phone 1302 and an external microphone 1303. The smart phone 1302 may represent one of the electronic devices 101, 102, 104 of FIG. 1. The microphone 1303 can be a stand-alone microphone, a headphone, an earbud, or the like. The microphone 1303 is communicatively coupled to the smart phone 1302 via a wired or wireless connection. Similar to the foldable device 1002 of FIG. 10, the smart phone 1302 is configured to conduct mobile spirometry by capturing and analyzing information associated with a user 1304, such as audio 1310 generated by the user 1304, a face image 1312 of the user 1304, and a face-to-phone distance 1314 or a face-to-microphone distance 1315.

The user 1304 conducts a pulmonary function test at home (or at another non-clinical location) using the smart phone 1302 and the external microphone 1303. To perform the test, the user 1304 holds the smart phone 1302 approximately 5-15 inches from the user's mouth facing the front camera 1318. The external microphone 1303 is placed at a similar distance in front of the user's mouth. When the external microphone 1303 comprises a headphone or earbud, the distance to the user's mouth is substantially fixed and is considered in the on-device spirometry test. The user 1304 inhales and exhales into the microphone 1303 while looking at the display of the smart phone 1302 and the camera 1318 to carry out the test. The smart phone 1302 measures air volume exchange during inhalation and exhalation of the user 1304 by analyzing the audio 1310 through the microphone 1303. In some embodiments, the smart phone 1302 can include multiple external microphones 1303 and multiple channels for recording audio. In such cases, the smart phone 1302 can perform a channel selection algorithm (such as described above) to identify the channel with the most reliable audio for analysis. The face-to-phone distance 1314 can be measured via a proximity sensor (similar to the proximity sensor 307 of FIG. 3), one or more motion sensors, by analyzing the face image 1312, using a depth camera, or using a combination of these. The smart phone 1302 can further analyze the amount of air volume exchange during the spirometry session to calculate one or more pulmonary function test parameters such as PEF, FEV1, FVC, and the like.

The data captured from the external microphone(s) 1303 is cross-correlated with the face image 1312 captured on the smart phone 1302, and the test events are aligned before further data processing. During the test, the smart phone 1302 can provide real-time feedback to guide the user 1304 to adjust the test, correct their effort, or to avoid mistakes. The smart phone 1302 can measure the effort of the user 1304 during the test using the user's audio 1310 and face image 1312. The smart phone 1302 can provide real-time feedback to the user 1304 in case the user 1304 needs to try harder or adjust their spirometry test. The feedback provided to the user 1304 can include visual feedback 1320 provided on the front display while the user 1304 is inhaling and exhaling. The visual feedback 1320 can include AR arrows that can indicate how much the user 1304 should widen or narrow their mouth during inhalation or exhalation for a proper test. Haptic feedback 1322 or audio feedback 1324 can be provided during the test to motivate the user 1304 to increase their effort by blowing more quickly or fully emptying their lungs. After the test is finished and validated, the results of the pulmonary function test are provided on the display of the smart phone 1302 as numerical values or demonstrated in a chart. The smart phone 1302 can utilize the user's data during the test to identify mistakes made by the user 1304. The mistakes can be displayed as warnings so that the user 1304 can correct their effort for later attempts. The user 1304 can regularly take the test using the smart phone 1302 and external microphone(s) 1303 in a convenient location, and clinicians can remotely track the results and the user's lung function to monitor their recovery or worsening of symptoms.

Figure 14:
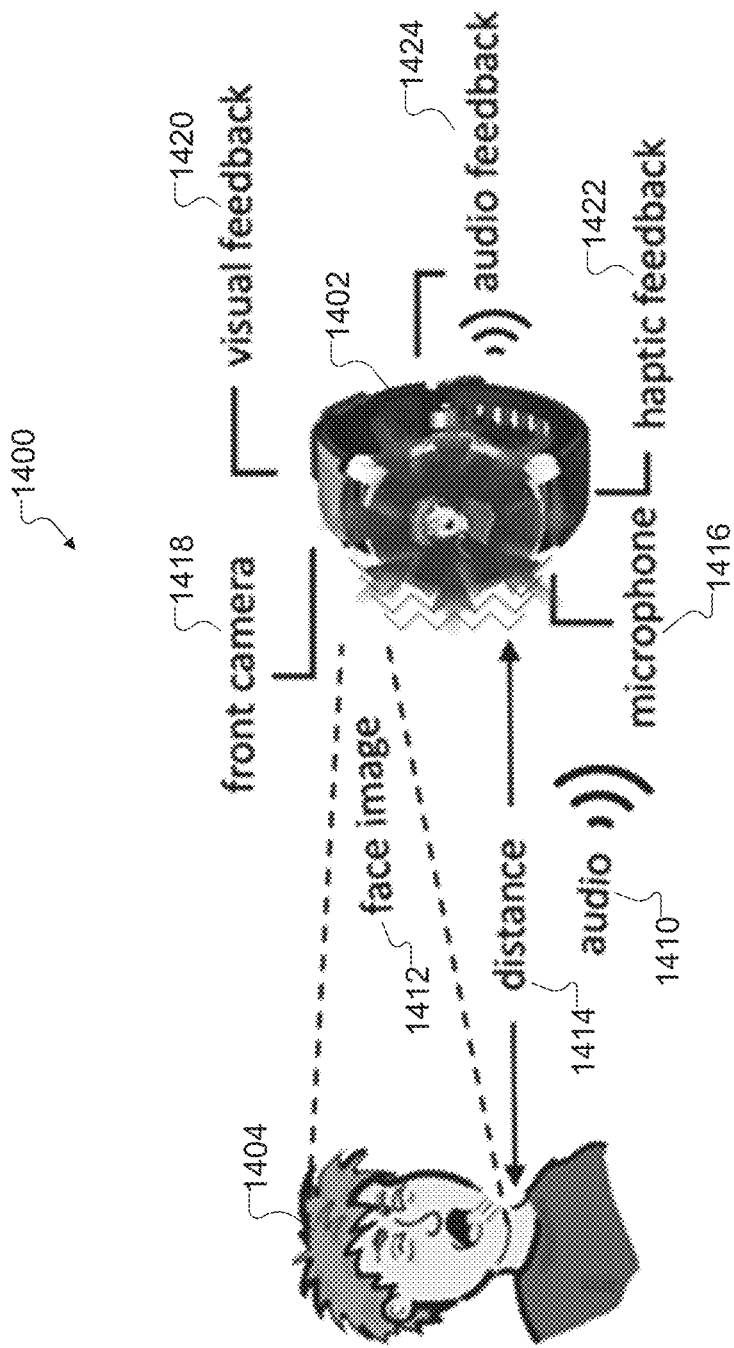

FIG. 14 illustrates an example system 1400 for performing an on-device spirometry test using a smart watch, in accordance with this disclosure. For ease of explanation, the system 1400 is described as involving at least one electronic device (such as the electronic device 101 of FIG. 1). However, the system 1400 could involve any other suitable device(s) or system(s) without departing from the scope of this disclosure.

As shown in FIG. 14, the system 1400 includes a smart watch 1402. The smart watch 1402 may represent one of the electronic devices 101, 102, 104 of FIG. 1. Similar to the foldable device 1002 of FIG. 10, the smart watch 1402 is configured to conduct mobile spirometry by capturing and analyzing information associated with a user 1404, such as audio 1410 generated by the user 1404, a face image 1412 of the user 1404, and a face-to-watch distance 1414.

The user 1204 conducts a pulmonary function test at home (or at another non-clinical location) using the smart watch 1402. To perform the test, the user 1404 holds the smart watch 1402 approximately 5-15 inches from the user's mouth facing the camera 1418 of the smart watch 1402, then inhales and exhales into a microphone 1416 located in or around the smart watch 1402. The smart watch 1402 measures air volume exchange during inhalation and exhalation of the user 1404 by analyzing the audio 1410 through the microphone 1416. In some embodiments, the smart watch 1402 can include multiple microphones 1416 and multiple channels for recording audio. In such cases, the smart watch 1402 can perform a channel selection algorithm (such as described above) to identify the channel with the most reliable audio for analysis. The face-to-watch distance 1414 can be measured via a proximity sensor (similar to the proximity sensor 307 of FIG. 3), one or more motion sensors, by analyzing the face image 1412, using a depth camera, or using a combination of these. The smart watch 1402 can further analyze the amount of air volume exchange during the spirometry session to calculate one or more pulmonary function test parameters such as PEF, FEV1, FVC, and the like.

During the test, the smart watch 1402 can provide real-time feedback to guide the user 1404 to adjust the test, correct their effort, or to avoid mistakes. The smart watch 1402 can measure the effort of the user 1404 during the test using the user's audio 1410 and face image 1412. The smart watch 1402 can provide real-time feedback to the user 1404 in case the user 1404 needs to try harder or adjust their spirometry test. The feedback provided to the user 1404 can include visual feedback 1420 provided on the watch display while the user 1404 is inhaling and exhaling. The visual feedback 1420 can include AR arrows that can indicate how much the user 1404 should widen or narrow their mouth during inhalation or exhalation for a proper test. Haptic feedback 1422 or audio feedback 1424 can be provided during the test to motivate the user 1404 to increase their effort by blowing more quickly or fully emptying their lungs. After the test is finished and validated, the results of the pulmonary function test are provided on the display of the smart watch 1402 as numerical values or demonstrated in a chart. The smart watch 1402 can utilize the user's data during the test to identify mistakes made by the user 1404. The mistakes can be displayed as warnings so that the user 1404 can correct their effort for later attempts. The user 1404 can regularly take the test on the smart watch 1402 in a convenient location, and clinicians can remotely track the results and the user's lung function to monitor their recovery or worsening of symptoms.

Although FIGS. 10 through 14 illustrate examples of systems for performing an on-device spirometry test, various changes may be made to FIGS. 10 through 14. For example, the systems 1000, 1100, 1200, 1300, 1400 could be implemented in any suitable manner, such as entirely within one electronic device or using a combination of devices. As a particular example, at least some of the functions and operations can be implemented or supported using one or more software applications or other software instructions that are executed by one or more processor(s) 120, 240 of the electronic device(s). In other embodiments, at least some of the functions and operations can be implemented or supported using dedicated hardware components. In general, the functions and operations can be performed using any suitable hardware or any suitable combination of hardware and software/firmware instructions. In some embodiments, the electronic device(s) could collect the audio, image, and proximity data and provide the data to a server 106, which could then perform some of the operations of FIGS. 10 through 14. Results of the processing could then be made available to the electronic device(s) and/or one or more other devices. In general, computing and communication systems come in a wide variety of configurations, and FIGS. 10 through 14 do not limit the scope of this disclosure to any particular configuration.

Figure 15:
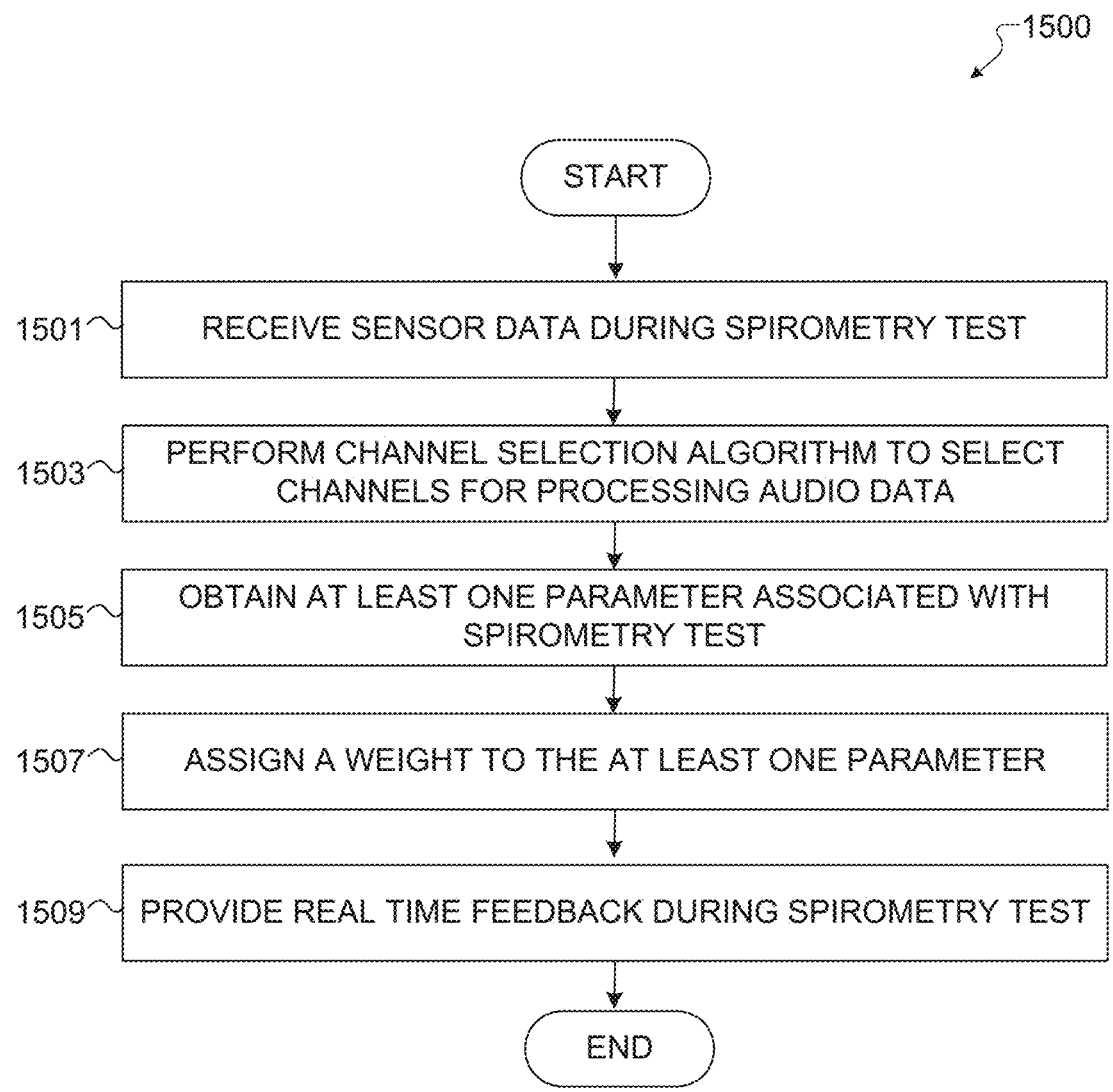
FIG. 15 illustrates an example method for measuring effort and providing feedback to a user during an on-device spirometry test in accordance with this disclosure.

FIG. 15 illustrates an example method 1500 for measuring effort and providing feedback to a user during an on-device spirometry test in accordance with this disclosure. For ease of explanation, the method 1500 shown in FIG. 15 is described as involving the use of the mobile device 305 of FIG. 3. However, the method 1500 shown in FIG. 15 could be used with any other suitable electronic device and in any suitable system, including any of the devices shown in FIGS. 10 through 14. Those of skill in the art will recognize that some or all of the operations of the method 1500 can be performed in conjunction with the method 700 of FIG. 7.

At operation 1501, the mobile device 305 receives sensor data during a spirometry test of a user. The sensor data includes audio data of the user, image data of the user's face, and distance data of a distance from the user's face to the mobile device 305 or an external microphone. This can include, for example, the mobile device 305 receiving audio data from the audio sensor 306, receiving distance data from the proximity sensor 307, and receiving image data of the face of the user from the image sensor 308.

At operation 1503, when the audio data of the user includes multiple channels of audio received by multiple microphones, the mobile device 305 performs a channel selection algorithm to select one or more channels for processing of the audio data. This can include, for example, the mobile device 305 performing the channel selection algorithm to select the one or more channels based on a sound intensity of the audio data, a sound envelope of the audio data, a position of the mobile device 305 relative to the user, an orientation of the mobile device 305 relative to the user, or a combination of these.

At operation 1505, the mobile device 305 obtains at least one measured parameter associated with the spirometry test. The at least one measured parameter is determined using at least one of the audio data, the image data, or the distance data. The at least one measured parameter is correlated with an amount of air volume exchange or an amount of exhalation force by the user during the spirometry test. This can include, for example, the mobile device 305 obtaining a shape or area of the user's mouth, a skin color of the user's face, a shape or size of the user's eye(s), a shape of the user's cheeks, an energy level of an audio feature, a duration of the audio feature, a frequency of the audio feature, a TTPF value, any other suitable measured parameter, or a combination of these.

At operation 1507, the mobile device 305 can optionally assign a weight to the at least one measured parameter. This can include, for example, the mobile device 305 assigning the weight based on at least one of an angle, an orientation, or a position of the mobile device 305 relative to the user. The weight correlates to an availability, accuracy, or reliability of the at least one measured parameter.

At operation 1509, the mobile device 305 provides real time feedback during the spirometry test. The real time feedback is based on the at least one measured parameter, and indicates whether or not the user is performing the spirometry test correctly. This can include, for example, the mobile device 305 providing visual feedback displayed on a display of the mobile device 305, haptic feedback generated by the mobile device 305, audio feedback generated by the mobile device 305, or a combination of these.

Although FIG. 15 illustrates one example of a method 1500 for measuring effort and providing feedback to a user during an on-device spirometry test, various changes can be made to FIG. 15. For example, various steps in FIG. 15 could overlap, occur in parallel, occur serially, occur in a different order, or occur any number of times. Also, various steps could be removed and/or other steps could be added. In addition, the steps of the method 1500 could be implemented in any suitable manner, such as entirely within the mobile device 305 or using a combination of devices. For instance, as indicated above, the mobile device 305 could collect data and provide the data to a server 106, which could then process the data and generate any suitable output.

Although this disclosure has been described with reference to various example embodiments, various changes and modifications may be suggested to one skilled in the art. It is intended that this disclosure encompass such changes and modifications as fall within the scope of the appended claims.

What is claimed is:

1. A method, comprising:
receiving, by an electronic device during a spirometry test of a user, audio data of the user from at least one audio sensor of the electronic device, image data of a face of the user from at least one image sensor of the electronic device, and distance data from at least one proximity sensor of the electronic device, the distance data indicating a distance from the face of the user to the electronic device;
obtaining, by the electronic device, at least one measured parameter associated with the spirometry test that is determined as a function of the audio data, the image data, and the distance data, wherein the at least one measured parameter is correlated with an amount of air volume exchange or an amount of exhalation force by the user during the spirometry test; and
providing, by the electronic device, real time feedback during the spirometry test, the real time feedback based on the at least one measured parameter, the real time feedback indicating whether or not the user is performing the spirometry test correctly.

2. The method of claim 1, wherein the at least one measured parameter comprises at least one of:
a shape of a mouth of the user, an area of the mouth of the user, a skin color of the face of the user, a shape of an eye of the user, a size of the eye of the user, a shape of cheeks of the user, an energy level of an audio feature obtained from the audio data, a duration of the audio feature, a frequency of the audio feature, or a time-to-peak-flow (TTPF).

3. The method of claim 1, wherein the real time feedback comprises at least one of visual feedback displayed on a display of the electronic device, haptic feedback generated by the electronic device, or audio feedback generated by the electronic device.

4. The method of claim 1, further comprising:
assigning, by the electronic device, a weight to the at least one measured parameter based on at least one of an angle, an orientation, or a position of the electronic device relative to the user, wherein the weight correlates to an availability, accuracy, or reliability of the at least one measured parameter.

5. The method of claim 1, wherein the audio data of the user comprises multiple channels of audio received by multiple microphones, the method further comprising:
performing, by the electronic device, a channel selection algorithm to select one or more of the channels for processing of the audio data, wherein the channel selection algorithm selects the one or more channels for processing of the audio data based on at least one of a sound intensity of the audio data, a sound envelope of the audio data, a position of the electronic device relative to the user, or an orientation of the electronic device relative to the user.

6. The method of claim 5, wherein:
the electronic device comprises a foldable smart phone, and
the channel selection algorithm selects the one or more channels for processing of the audio data further based on a fold angle of the foldable smart phone.

7. The method of claim 1, wherein:
the at least one audio sensor comprises an external microphone; and
the electronic device is communicatively coupled to the external microphone.

8. The method of claim 1, further comprising:
estimating, by the electronic device, a probability that the user is maximizing the amount of air volume exchange during the spirometry test or a probability that the user is maximizing the amount of exhalation force during the spirometry test.

9. An electronic device comprising:
multiple sensors comprising at least one audio sensor, at least one image sensor, and at least one proximity sensor; and
a processor configured to:
receive, during a spirometry test of a user, audio data of the user from the at least one audio sensor, image data of a face of the user from the at least one image sensor, and distance data from the at least one proximity sensor, the distance data indicating a distance from the face of the user to the electronic device;
obtain at least one measured parameter associated with the spirometry test that is determined as a function of the audio data, the image data, and the distance data, wherein the at least one measured parameter is correlated with an amount of air volume exchange or an amount of exhalation force by the user during the spirometry test; and
control the electronic device to provide real time feedback during the spirometry test, the real time feedback based on the at least one measured parameter, the real time feedback indicating whether or not the user is performing the spirometry test correctly.

10. The electronic device of claim 9, wherein the at least one measured parameter comprises at least one of:
a shape of a mouth of the user, an area of the mouth of the user, a skin color of the face of the user, a shape of an eye of the user, a size of the eye of the user, a shape of cheeks of the user, an energy level of an audio feature obtained from the audio data, a duration of the audio feature, a frequency of the audio feature, or a time-to-peak-flow (TTPF).

11. The electronic device of claim 9, wherein the real time feedback comprises at least one of visual feedback displayed on a display of the electronic device, haptic feedback generated by the electronic device, or audio feedback generated by the electronic device.

12. The electronic device of claim 9, wherein the processor is further configured to:
assign a weight to the at least one measured parameter based on at least one of an angle, an orientation, or a position of the electronic device relative to the user, wherein the weight correlates to an availability, accuracy, or reliability of the at least one measured parameter.

13. The electronic device of claim 9, wherein:
the audio data of the user comprises multiple channels of audio received by multiple microphones, and
the processor is further configured to perform a channel selection algorithm to select one or more of the channels for processing of the audio data, wherein the channel selection algorithm selects the one or more channels for processing of the audio data based on at least one of a sound intensity of the audio data, a sound envelope of the audio data, a position of the electronic device relative to the user, or an orientation of the electronic device relative to the user.

14. The electronic device of claim 13, wherein:
the electronic device comprises a foldable smart phone, and
the channel selection algorithm selects the one or more channels for processing of the audio data further based on a fold angle of the foldable smart phone.

15. The electronic device of claim 9, wherein:
the at least one audio sensor comprises an external microphone; and
the electronic device is communicatively coupled to the external microphone.

16. The electronic device of claim 9, wherein the processor is further configured to:
estimate a probability that the user is maximizing the amount of air volume exchange during the spirometry test or a probability that the user is maximizing the amount of exhalation force during the spirometry test.

17. A non-transitory computer readable medium containing computer readable program code that, when executed, causes at least one processor of an electronic device to:
receive, during a spirometry test of a user, audio data of the user from at least one audio sensor of the electronic device, image data of a face of the user from at least one image sensor of the electronic device, and distance data from at least one proximity sensor of the electronic device, the distance data indicating a distance from the face of the user to the electronic device;
obtain at least one measured parameter associated with the spirometry test that is determined as a function of the audio data, the image data, and the distance data, wherein the at least one measured parameter is correlated with an amount of air volume exchange or an amount of exhalation force by the user during the spirometry test; and
control the electronic device to provide real time feedback during the spirometry test, the real time feedback based on the at least one measured parameter, the real time feedback indicating whether or not the user is performing the spirometry test correctly.

18. The non-transitory computer readable medium of claim 17, wherein the at least one measured parameter comprises at least one of: a shape of a mouth of the user, an area of the mouth of the user, a skin color of the face of the user, a shape of an eye of the user, a size of the eye of the user, a shape of cheeks of the user, an energy level of an audio feature obtained from the audio data, a duration of the audio feature, a frequency of the audio feature, or a time-to-peak-flow (TTPF).

19. The non-transitory computer readable medium of claim 17, wherein the real time feedback comprises at least one of visual feedback displayed on a display of the electronic device, haptic feedback generated by the electronic device, or audio feedback generated by the electronic device.

20. The non-transitory computer readable medium of claim 17, wherein the computer readable program code further causes the at least one processor to:
  assign a weight to the at least one measured parameter based on at least one of an angle, an orientation, or a position of the electronic device relative to the user, wherein the weight correlates to an availability, accuracy, or reliability of the at least one measured parameter.

* * * * *